US012426976B2

United States Patent
Solomon et al.

(10) Patent No.: US 12,426,976 B2
(45) Date of Patent: Sep. 30, 2025

(54) USER INTERFACE FOR CONTROLLING A SURGICAL SYSTEM

(71) Applicant: BEYEONICS SURGICAL LTD., Haifa (IL)

(72) Inventors: Yaara Solomon, Haifa (IL); Rani Ben-Yishai, Haifa (IL)

(73) Assignee: BEYEONICS SURGICAL LTD., Haifa (IL)

( * ) Notice: Subject to any disclaimer, the term of this patent is extended or adjusted under 35 U.S.C. 154(b) by 440 days.

(21) Appl. No.: 17/858,585

(22) Filed: Jul. 6, 2022

(65) Prior Publication Data
US 2022/0331038 A1    Oct. 20, 2022

Related U.S. Application Data

(63) Continuation of application No. PCT/IL2021/050023, filed on Jan. 6, 2021.
(Continued)

(51) Int. Cl.
*A61B 34/00* (2016.01)
*G02B 27/00* (2006.01)
(Continued)

(52) U.S. Cl.
CPC .......... *A61B 34/74* (2016.02); *G02B 27/0093* (2013.01); *G02B 27/0172* (2013.01);
(Continued)

(58) Field of Classification Search
CPC ........................ A61B 34/74; G02B 27/0093; G02B 27/0172; G06F 3/012; G06F 3/017; G06F 3/023
(Continued)

(56) References Cited

U.S. PATENT DOCUMENTS 5,436,542 A * 7/1995 Petelin ................... B25J 9/1679
                                                            318/567
9,529,200 B2   12/2016 Thurber et al.
(Continued)

FOREIGN PATENT DOCUMENTS

CN        108289600         7/2018
CN        209770538        12/2019
(Continued)

OTHER PUBLICATIONS

International Search Report for PCT Application No. PCT/IL2021/050023, mailed May 25, 2021.
(Continued)

*Primary Examiner* — Mohammad Ali
*Assistant Examiner* — Joshua T Sanders
(74) *Attorney, Agent, or Firm* — PEARL COHEN ZEDEK LATZER BARATZ LLP

(57) ABSTRACT

A user interface for enabling and controlling functions of a surgical system, comprising: a foot-operated function switch configured to be switched to any one of multiple discrete states by the user's foot; a head tracker configured to track the user's head motions; and a processor coupled to the function switch and head tracker, and configured to: obtain an association between a plurality of sequences comprising at least one of the multiple discrete states, and a plurality of corresponding system functions of the surgical system, receive an indication of at least one of the discrete states from the function switch, identify a system function based on the indication and the association, receive a head motion from the head tracker, and apply the head motion to control the identified system function of the surgical system.

18 Claims, 28 Drawing Sheets

Related U.S. Application Data

(60) Provisional application No. 63/104,531, filed on Oct. 23, 2020, provisional application No. 62/957,341, filed on Jan. 6, 2020.

(51) Int. Cl.
*G02B 27/01* (2006.01)
*G06F 3/01* (2006.01)
*G06F 3/023* (2006.01)

(52) U.S. Cl.
CPC .............. *G06F 3/012* (2013.01); *G06F 3/017* (2013.01); *G06F 3/023* (2013.01); *A61B 2560/0487* (2013.01)

(58) Field of Classification Search
USPC .......................................................... 700/83
See application file for complete search history.

(56) References Cited

U.S. PATENT DOCUMENTS

| | | | | |
|---|---|---|---|---|
| 2004/0169673 | A1* | 9/2004 | Crampe | A61B 34/20 600/300 |
| 2005/0086611 | A1* | 4/2005 | Takabe | G06F 3/0482 715/830 |
| 2015/0051607 | A1* | 2/2015 | Hajishah | G05G 1/445 341/20 |
| 2019/0008595 | A1* | 1/2019 | Popovic | A61B 34/20 |
| 2019/0354200 | A1 | 11/2019 | Rapoport | |

FOREIGN PATENT DOCUMENTS

| | | |
|---|---|---|
| GB | 2311362 | 9/1997 |
| WO | WO 9735277 | 9/1997 |
| WO | WO 2018/067611 | 4/2018 |
| WO | WO 2020/084625 | 4/2020 |

OTHER PUBLICATIONS

Mak Yoeko, "Head Motion Controlled Endoscopic Camera Manipulation using Inertial Motion Sensor and Mixed Reality Headset", Dec. 1, 2018, University of Twente; Retrived from: https://essay.utwente.nl/94665/1/Mak_MA_EEMCS.pdf.

* cited by examiner

USER INTERFACE FOR CONTROLLING A SURGICAL SYSTEM

CROSS REFERENCE TO RELATED APPLICATIONS

This Application is a Continuation of International Application No. PCT/IL2021/050023, filed on Jan. 6, 2021, which claims the benefit of U.S. Provisional Patent Application No. 62/957,341 filed on Jan. 6, 2020 and of U.S. Provisional Patent Application No. 63/104,531 filed on Oct. 23, 2020, all of which are incorporated herein by reference in their entireties.

FIELD OF THE DISCLOSED TECHNIQUE

The disclosed technique relates to surgical systems in general, and to methods and systems for enabling and controlling system functions of a surgical system during surgical procedures, in particular.

BACKGROUND OF THE DISCLOSED TECHNIQUE

Head mounted display (HMD) systems for surgical applications allow for a comfortable and intuitive method to control many, if not most system aspects, by using head gestures. In order to avoid unintentional control of a system function due to spontaneous or unintentional head movements, head gestures may be enabled by a footswitch command In addition to enabling one or more head gestures, the footswitch command may also allow the user to select the enabled system function.

Current solutions for selection and enablement of a system function are based on a footswitch with multiple control modalities, such as buttons, pedals, joysticks and the like. Each control modality enables a different function. Standard footswitches may comprise two or more pedals, each having two pressing options (i.e. pressing with the forefoot or pressing with the heel), six discrete buttons, and a joystick. Since the user's eyes are focused on the surgical field, the user must remember the footswitch layout. The user often operates barefoot to facilitate groping the footswitch to identify the various control modalities.

Some solutions for simplifying the footswitch and reducing the number of required control modalities employ multiple system modes. The configuration of the various control modalities is then changed according to the current system mode. This reduces the number of required control modalities, as not all system functions are required to be enabled in a specific system mode. Therefore, a single control modality may enable different functions in different system modes.

Additional solutions include using different head gestures for controlling different functions enabled by a single control modality. For instance, a single button may enable controlling focus with up-down head gestures and controlling zoom by left-right head gestures.

Other solutions for simplifying the footswitch include allowing the user to use a combination of control modalities to enable a function. For example, one button may be configured to enable function #1, a second button may be configured to enable function #2, and simultaneously pressing the two buttons may be configured to enable function #3.

In addition, current solutions include displaying, via the HMD, the layout of the footswitch and the currently pressed button (or pedal, etc.). This enables the user to see which control modality is being pressed before commencing the head gesture and adjust the selection of the control modality if it was wrongly identified.

SUMMARY OF THE PRESENT DISCLOSED TECHNIQUE

It is an object of the disclosed technique to provide a novel method and system for enabling and controlling functions of a surgical system.

There is provided, in accordance with an embodiment, a user interface for enabling and controlling functions of a surgical system, comprising: a foot-operated function switch configured to be switched to any one of multiple discrete states by the foot of a user; a head tracker configured to track head motions of the user; and a processor coupled to the foot-operated function switch and the head tracker, and configured to: obtain an association between a plurality of sequences comprising at least one of the multiple discrete states and a plurality of corresponding system functions of the surgical system, receive an indication of at least one of the multiple discrete states from the function switch, identify a system function based on the received indication and the association, receive a head motion tracked by the head tracker, and apply the head motion to control the identified system function of the surgical system.

In some embodiments, the user interface further comprises determining a performed sequence from the at least one received indication.

In some embodiments, the foot-operated function switch provides a single point of contact with the foot of the user allowing to switch between the multiple discrete states while maintaining continuous contact with the foot of the user via the single point of contact.

In some embodiments, the foot-operated function switch has at least one of a rotational degree of freedom and a tilt degree of freedom.

In some embodiments, the foot-operated function switch comprises a component selected from the group consisting of: a pedal, a footrest, a joystick, a ball held within a socket, an inertial measuring unit, a micro-switch, and an opto switch.

In some embodiments, the user interface further comprises an HMD, wherein the processor is further configured to display the identified system function via the HMD.

In some embodiments, the processor is further configured to continually receive updated indications of at least one of the multiple discrete states from the function switch, continually determine the performed sequence based on the updated indications, and continually identify the system function based on the determined performed sequence until the head motion is received from the head tracker.

In some embodiments, upon receiving the head motion, the processor is further configured to cease determining the performed sequence and identifying the system function and initiate applying the head motion to control the identified system function.

In some embodiments, the at least one processor is further configured to ignore subsequently received indications from the function switch while applying the head motion to control the identified system function.

In some embodiments, the at least one processor is further configured to determine that the head of the user is stationary and deactivate the function switch in response.

In some embodiments, the at least one processor is further configured to cease applying the head motion to control the identified system function after at least one of: a lapse of a predefined time threshold, and the deactivation of the function switch.

There is provided, in accordance with another embodiment, a method for enabling and controlling functions of a surgical system, comprising: obtaining an association between a plurality of sequences and a plurality of corresponding system functions of the surgical system, the sequences comprising at least one of multiple discrete states for a foot-operated function switch, wherein the foot-operated function switch is configured to be switched to any the multiple discrete states by the foot of a user; receiving an indication of at least one of the multiple discrete states from the function switch; identifying a system function based on the performed sequence and the association; receiving a head motion tracked by a head tracker; and applying the head motion to control the identified system function of the surgical system.

In some embodiments, the method further comprises determining a performed sequence from the received indication.

In some embodiments, the performed sequence is determined from multiple indications of the discrete states from the function switch.

In some embodiments, applying the head motion to control the identified system function is manifested in a displayed image.

In some embodiments, applying the head motion to control the identified system function is manifested in an image acquired by a camera of the surgical system.

In some embodiments, at least one of the plurality of sequences is characterized by a feature selected from the group consisting of: one of the multiple discrete states, a predefined duration of one of the multiple discrete states, a subset of the multiple discrete states, an ordered subset of the multiple discrete states, and a repetition of one or more of the multiple discrete states.

In some embodiments, the method further comprises continually receiving updated indications of at least one of the multiple discrete states from the function switch, continually determining the performed sequence based on the updated indications, and continually identifying the system function based on the determined performed sequence until the head motion is received from the head tracker.

In some embodiments, the method further comprises ceasing the continually determining the performed sequence and the continually identifying the system function after receiving the head motion from the head tracker and initiating the applying the head motion to control the identified system function.

In some embodiments, the method further comprises ignoring subsequently received indications from the function switch while applying the head motion to control the identified system function.

In some embodiments, the method further comprises determining that the head of the user is stationary and deactivating the function switch in response.

In some embodiments, the method further comprises ceasing to apply the head motion to control the identified system function after at least one of: a lapse of a predefined time threshold, and the deactivation of the function switch.

There is provided, in accordance with another embodiment, a user interface for enabling and controlling functions of a surgical system, comprising: a function switch configured to sense lower body motion of at least one lower body part of a user; a head tracker configured to track head motion of the user; and a processor coupled to the function switch and the head tracker, and configured to: obtain an association between a plurality of predefined lower body motion sequences and a plurality of corresponding system functions of the surgical system, receive the sensed lower body motion from the function switch, determine a lower body motion sequence from the sensed lower body motion of at least one lower body part of the user, identify one of the plurality of predefined lower body motion sequences based on the determined lower body motion sequence, identify a system function based on the identified one of the plurality of predefined lower body motion sequences and the association, receive a head motion tracked by the head tracker, and apply the head motion to control the identified system function of the surgical system.

In some embodiments, the at least one lower body part of the user is one or more of: a toe, a foot, a leg, a knee, a hip, and a waist of the user.

In some embodiments, the at least one processor is further configured to display the identified system function.

In some embodiments, the user interface further comprises a head mounted display (HMD) system, wherein the identified system function is displayed via the HMD.

In some embodiments, the head tracker is integrated with the HMD.

In some embodiments, the user interface further comprises a camera, wherein applying the head motion to control the identified system function is manifested in an image acquired by the camera.

In some embodiments, the function switch is further configured to sense the lower body motions along at least one degree of freedom.

In some embodiments, the identified one of the plurality of predefined lower body motion sequences comprises an accumulation of one or more lower body motions.

In some embodiments, the processor is further configured to continually update the identified system function based on the sensed lower body motion until the processor receives the head motion, and, upon receiving the head motion, suspend the updating the identified system function and initiate the applying the head motion to control the identified system function.

In some embodiments, the at least one processor is further configured to ignore subsequently sensed lower body motions while applying the head motion to control the identified system function of the surgical system.

In some embodiments, the at least one processor is further configured to cease applying the head motion to control the identified system function of the surgical system after determining at least one of: a stationary head for a predefined time threshold, and a deactivation indication from the function switch.

There is provided, in accordance with another embodiment, a method for enabling and controlling functions of a surgical system, comprising the procedures of: obtaining an association between a plurality of predefined lower body motion sequences and a plurality of corresponding system functions of the surgical system; obtaining a sensed lower body motion of at least one lower body part of the user from a function switch; determining a lower body motion sequence from the sensed lower body motion of the at least one lower body part of the user; identifying one of the plurality of predefined lower body motion sequences based on the determined lower body motion sequence; identifying a system function based on the identified one of the plurality of predefined lower body motion sequences and the association; receiving a head motion from a head tracker; and applying the head motion to control the identified system function of the surgical system.

In some embodiments, the lower body motion is at least one of: a tilt, a rotation, a lift, a drop, a turn, a swinging motion, a push, a pull, a twist, a drag, a tap, a press and a swipe motion.

In some embodiments, the at least one lower body part is one or more of: a toe, a foot, a leg, a knee, a hip, and a waist of the user.

In some embodiments, the head tracker is selected from the group consisting of: an inertial measuring unit, a camera, an acoustic sensor, a tactile sensor, and an electromagnetic sensor, and wherein the head tracker is any of: a wearable head tracker worn by the user, and a non-wearable head tracker positioned within a trackable range of the user.

In some embodiments, the method further comprises displaying the identified system function.

In some embodiments, the identified system function is displayed via a head mounted display (HMD) worn by the user.

In some embodiments, applying the head motion to control the identified system function is manifested in an image displayed via the HMD.

In some embodiments, applying the head motion to control the identified system function is manifested in an image acquired by a camera system of the surgical system.

In some embodiments, the sensed lower body motion is sensed by the function switch along at least one degree of freedom.

In some embodiments, the determined one of the plurality of predefined lower body motion sequences comprises an accumulation of multiple sensed lower body motions.

In some embodiments, the method further comprises continually updating the identified system function based on the sensed lower body motion until the head motion is received, and upon receiving the head motion, suspending updating the identified system function and initiating the applying the head motion to control the identified system function.

In some embodiments, the method further comprises ignoring subsequently sensed lower body motions while applying the head motion to control the identified system function of the surgical system.

In some embodiments, the method further comprises determining a stationary state for the head of the user for a first predefined time threshold and deactivating the function switch in response.

In some embodiments, the method further comprises ceasing to apply the head motion to control the identified system function of the surgical system after at least one of: a lapse of a second predefined time threshold, and the deactivation of the function switch.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1A:
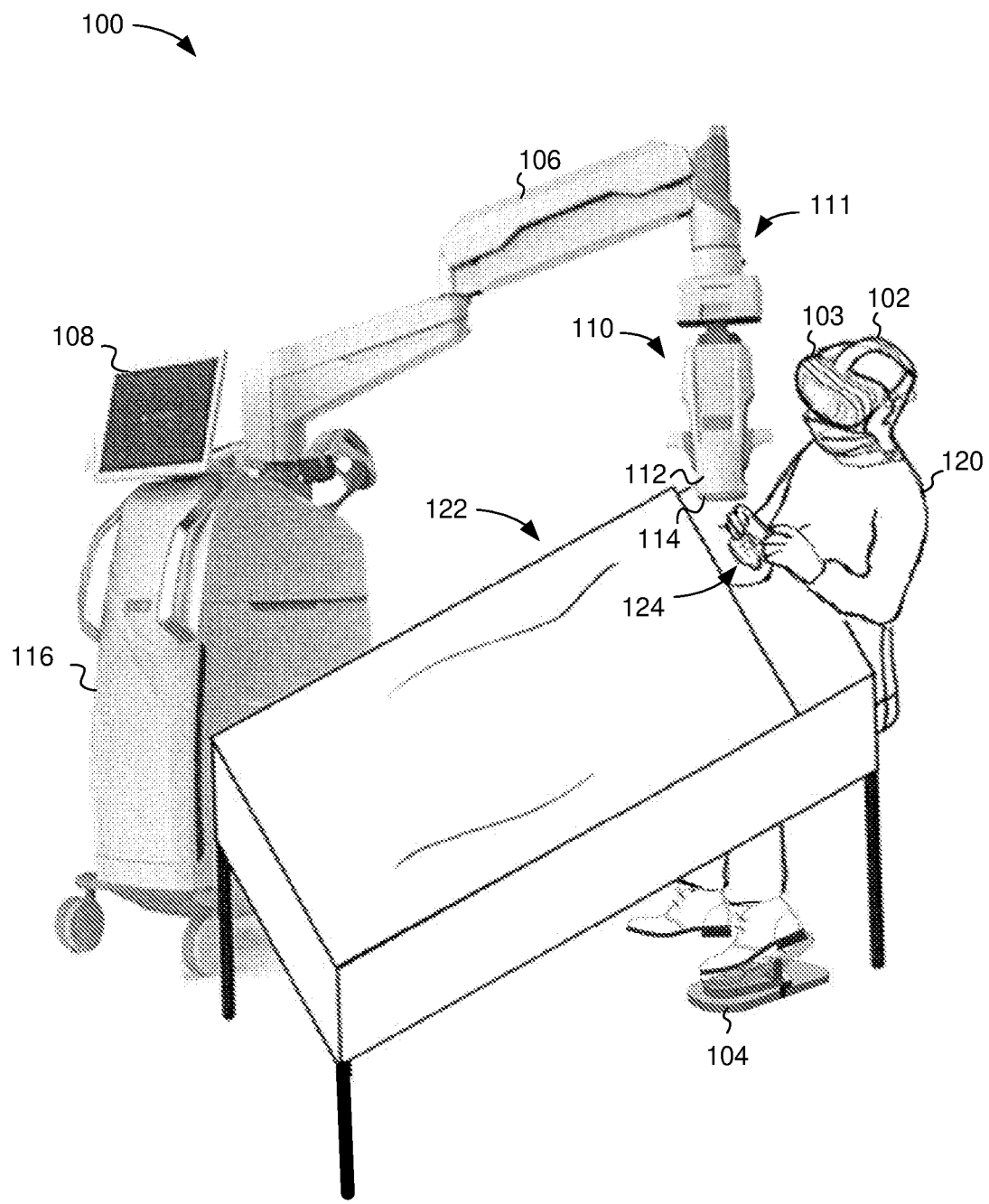
FIG. 1A-1D, taken together, is a schematic illustration of an exemplary user interface for enabling and controlling functions of a surgical system, constructed and operative in accordance with an embodiment of the disclosed technique.

The disclosed technique overcomes the disadvantages of the prior art by providing a user interface comprising a function switch for controlling a surgical system. The function switch simplifies the user interface by reducing the number of control modalities needed for enabling various system functions. The function switch allows the user to select from a wide range of system functions via a relatively simple user interface, sparing the user from having to memorize a complicated device layout. The function switch may be implemented in a variety of ways, and may be used in conjunction with other user input means to control the surgical system, such as head motions, (e.g. gestures), and the like. In one embodiment, the function switch is operated via the foot, allowing a surgeon to select from multiple system functions using only a few simple foot motions. The surgeon may operate the function switch while wearing shoes, since the simplified user interface of the function switch does not have multiple buttons that can require identifying with bare toes. In other embodiments, the function switch is any of: a wearable device, a device configured with a moveable chair, a touchpad, or combinations thereof.

The user input interface presented by the function switch provides a more intuitive user experience for the surgeon. The function switch described herein may be implemented with or without physical (i.e. mechanical) contact with the surgeon. In some embodiments, the function switch is implemented as a foot-operated device providing a single point of interface (i.e. physical contact) with the surgeon, such as with a single pedal, joystick, ball-and-socket, rotatable and tiltable footrest, and the like, obviating the need for multiple buttons to control multiple functions. The single mechanical interfacing component is maneuverable over a range of motions of at least one degree of freedom, replacing the multiple buttons and/or joysticks typical of conventional surgical foot switches. Thus, instead of navigating multiple buttons and switches, the surgeon maneuvers the single interfacing component with one or more rotations, tilts, presses, and the like, using the foot.

In some of the embodiments, the single interfacing component can be switched to any one of multiple discrete states by the foot of a user. Each discrete state can enable head gestures (e.g. head motions) for controlling a different function. Additionally or alternatively, different sequences of discrete states can enable different functions, which are then controllable with head gestures. The surgeon may perform a sequence of discrete states by maneuvering the single interfacing component into various states in a predetermined order. In some embodiments a sequence of discrete states includes only a single state. In some embodiments, a sequence includes multiple states. In some embodiments, a sequence of discrete states includes holding the single interfacing component in one or more particular states for specific periods of time (e.g. short press followed by a long press).

The function switch may include one or more sensors, such as micro-switches and/or opto-switches for determining the current state at any given point in time. The function switch may continuously communicate indications of the current state to the processor using conventional wired or wireless means. The processor identifies which system function to enable based on the received indications (e.g. one or more) by referencing a library associating multiple sequences, each including at least one discrete state, with multiple corresponding system functions. The processor may determine a sequence based on the received indications and match the sequence with multiple predefined sequences of discrete states stored in the library. In some embodiments, the indication of the current state is transmitted by the function switch an identifying number. In some embodiments the different states are enumerated and the function switch transmits one or more numbers to the processor to indicate the current state. In some embodiments, the function switch transmits two or more numbers to indicate the current state. For example, the first number represents a tilt state of a footrest coupled with the function switch (first degree of freedom), and a second number represents a rotation state of the footrest. Based on both numbers, the processor determines a current state of the footrest, e.g., tilt up and rotate left for the first state, and tilt up and rotate right for the second state.

In other embodiments, the function switch is implemented as a sensor or sensors that sense lower body motion, without using a maneuverable single interfacing component. The body motions of the surgeon can be motions of any of the foot, toe, leg, knee, hip, or waist, and can be sensed by various means, such as by a camera sensing visible and/or infrared wavelengths (e.g. a camera that images a user's foot and/or leg), a wearable inertial measurement unit ("IMU") (e.g. an IMU that is attached to a user's foot or leg, or to a chair the user is sitting on), a touchpad that senses motion of a surgeon's foot (e.g. tapping, dragging, pressing, lifting), and the like.

The function switch senses continuous lower body motions by the surgeon and provides the sensed motion to the processor using conventional wired or wireless communication. The processor analyzes the sensed motion to determine a corresponding system function of the surgical system. The processor enables the control of this function, e.g. via head gestures. For example, the processor associates a continuous clockwise rotation of the foot (first movement) with a first system function and a continuous counterclockwise rotation (second movement) with a second system function. Similarly, the processor associates a forward 10 degrees tilt of the foot, e.g. by raising the heel from the floor (third movement) with a third system function and a forward 20 degree tilt (fourth movement) with a fourth system function. The processor associates the different motions with the different system functions, allowing the surgeon to select from the multiple system functions using natural, intuitive motions. This frees the surgeon from having to search and grope between the different buttons and joysticks of conventional foot pedals, which are typically not in visible range of the surgeon. Additionally or alternatively, different motion sequences can enable head gestures for controlling different functions.

The term "motion sequence" as used herein is understood as a natural body movement which is sensed by a sensing device as a sequential progression of positions and orientations over time. A motion sequence may be a single movement (e.g. turn of the foot), or multiple movements (e.g. turn of the foot and lift of the heel). The function switch senses continuous lower body motions by the surgeon which is provided to a processor for analyzing. The processor compares the sensed motion sequence to a library of predefined motion sequences to determine a match and identify a corresponding system function.

In some embodiments, the function switch is used in conjunction with a head tracker configured with a head mounted display (HMD) for controlling parameters (e.g. functions) of the surgical system. The surgeon uses the function switch to select which system function to control (e.g. to enable the control of), and implements the actual control with head motions detected by the head tracker. While the description and illustrations that follow relate generally to a function switch implemented as a footswitch, and a head tracker integrated with an HMD, this is but an exemplary implementation that is not intended to limit the invention to this specific embodiment. It is to be noted that the function switch may be implemented in any number of ways, such as a wearable device configured to detect lower body motions of the wearer, joystick, lever, ball-and-socket mechanism, touchpad, and the like. Alternatively, the function switch may be implemented with a swivel chair. A user sitting in the chair may select control functions by rotating the chair with the body and/or tapping on the leg of the chair with the foot. In some embodiments, the head tracker may be provided to track the surgeon's head motions without an HMD. Importantly, the function switch is operated in a hands-free manner, freeing the surgeon's hands to perform the surgical procedure.

Reference is now made to FIGS. 1A-1D, which taken together, illustrate an exemplary user interface for enabling and controlling functions of a surgical system, generally referenced 100, constructed and operative in accordance with an embodiment of the disclosed technique. Although much of the description herein generally refers to the microscopy system shown in FIG. 1A, this illustration is given for exemplary purposes only, and is not intended to limit the invention to the specific features of this implementation. The invention may similarly be used for non-microscopy surgical systems, for example visor-guided surgery (VGS) systems. In VGS procedures, the HMD augments the surgeon's view of the patient and allows the surgeon to see anatomical features and surgical tools as if the patient's body were partially transparent. These procedures may optionally be performed entirely without a magnified image of the surgical field and therefore without a camera head unit.

Referring to FIG. 1A, system 100 includes a head tracker 102 integrated with an HMD 103, a function switch 104, an arm 106, a cart 116 housing a computer 118 (not shown) and supporting a screen 108, a camera head 110, and a camera head positioner 111. A surgeon 120 controls parameters and settings for system 100 via function switch 104 and head tracker 102, freeing his hands for the surgical procedure. While the embodiment shown in FIG. 1A shows head tracker 102 integrated with HMD 103, this is not required, and is not intended to limit the invention. It is to be understood that head tracker 102 may be implemented in any suitable manner known in the art, such as with one or more optical, inertial, mechanical, or acoustic (e.g. ultrasound) position and/or motion detectors that can operate independently from the display provided to present information to surgeon 120. Similarly, while function switch 104 is shown as a foot enabled switch, this too is not required, and is not intended to limit the invention, as will be described below.

Camera head 110 houses a camera system 112 and an illumination system 114. Camera system 112 may include at least two high resolution cameras (not shown). Arm 106 connects computer 118 to camera head positioner 111 and camera head 110. Computer 118 is electrically coupled to camera head positioner 111 (optional), camera head 110, camera system 112, and illumination system 114 via one or more wires and/or cables (not shown) integrated inside cart 116 and arm 106.

Computer 118 controls the position and orientation of camera head 110. Arm 106 may be a mechanical arm, in which case computer 118 control camera head 110 via camera head positioner 111 comprising multiple motors in the x, y, and z coordinates and optionally one or more motors for controlling tilt. Alternatively, arm 106 is robotic and computer 118 controls the position and orientation of camera head 110 by controlling arm 106. Computer 118 additionally controls operational parameters for illumination system 114 and camera system 112, details of which are provided below.

Head tracker 102, HMD 103, function switch 104, and computer 118 are each provided with one or more transmitters and/or receivers (not shown) for communicatively coupling there between. The transmitters and receivers may be compatible with any suitable wired and/or wireless communications means and protocols, such as an electric or fiber optic cable (not shown), Wifi, BlueTooth, ZigBee, short range, medium range, long range, and microwave RF, wireless optical means (e.g. laser, lidar, infrared), acoustic means, ultrasonic means, and the like.

Figure 1B:
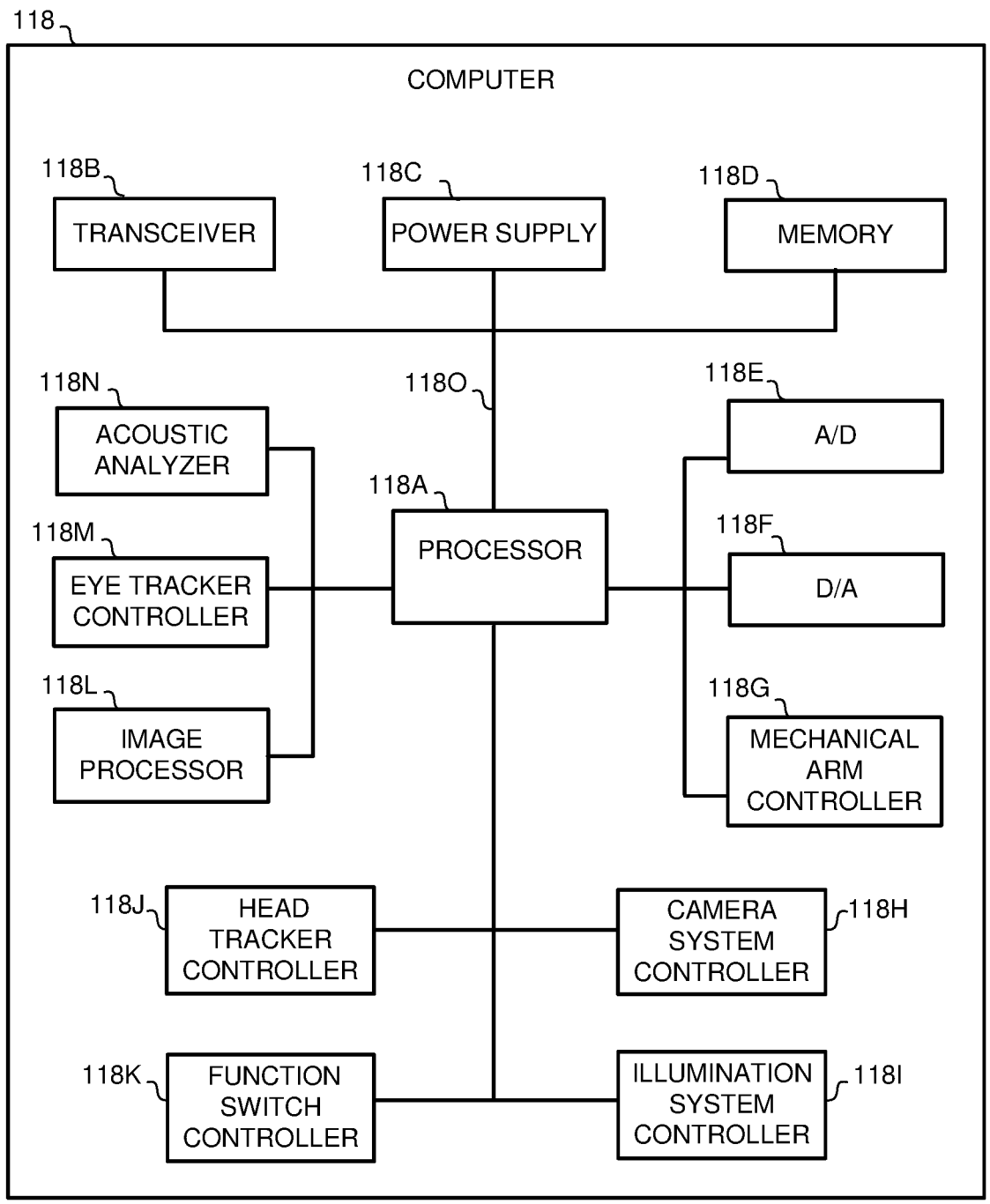

Referring to FIG. 1B, a schematic block diagram of computer 118 of FIG. 1A is shown. FIG. 1B is intended as an exemplary implementation and does not limit the invention to any specific hardware or software configuration. For example, software modules may replace hardware modules, and vice versa, where applicable. Computer 118 includes at least one processor 118A, at least one transceiver 118B, a power supply 118C, at least one memory 118D, at least one analog to digital A/D converter 118E, at least one digital to analog D/A converter 118F, and one or more of: a mechanical arm controller 118G, a camera system controller 118H, an illumination system controller 118I, a head tracker controller 118J, a function switch controller 118K, an image processor 118L, an eye tracker controller 118M, an acoustic analyzer 118N, and at least one bus 118O. At least one processor 118A may include any of a central processing unit (CPU), graphical processing unit (GPU), accelerated processing unit (APU), and the like. At least one processor 118A, transceiver 118B, power supply 118C, memory 118D, A/D converter 118E, D/A converter 118F, mechanical arm controller 118G, camera system controller 118H, illumination system controller 118I, head tracker controller 118J, function switch controller 118K, image processor 118L, eye tracker controller 118M, acoustic analyzer 118N are coupled via at least one bus 118O.

Although computer 118 is illustrated as a single unit, this is for conceptual purposes only. Computer 118 may be implemented as multiple distributed units that operate in a coordinated manner with system 100. For example, each of at least one processor 118A, transceiver 118B, power supply 118C, and memory 118D may include multiple processing units, memories, power supplies, and transceivers, respectively, that can be distributed among the components of system 100. For example, any of camera head 110, head tracker 102, function switch 104, a remote server (not shown), and the like, may each be provided with a processor, memory, and transceiver that operate in a coordinated manner to control system 100.

Figure 1C:
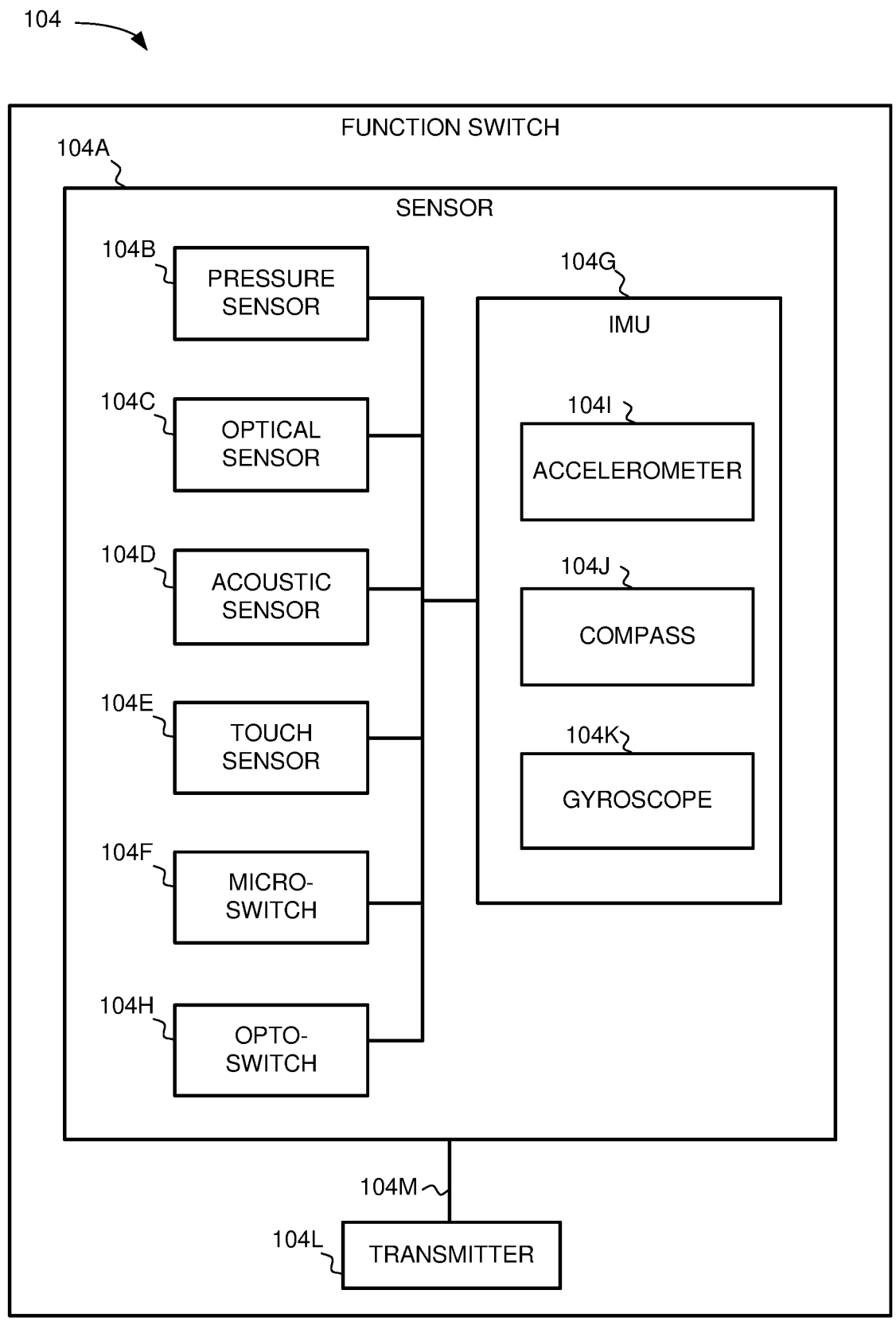

Referring to FIG. 1C, a schematic block diagram of a general function switch, such as function switch 104 of FIG. 1A is shown. FIG. 1C is an exemplary implementation for a general function switch and is not intended to limit the invention to a specific embodiment, nor to the specific modules shown. It is to be understood that any suitable sensory component known in the art may be used, and the invention is not limited to the specific sensory components listed herein. Similarly, software modules may replace hardware modules, and vice versa. Function switch 104 includes a sensor unit 104A for sensing motions and/or for allowing to determine discrete states, as described above. Thus, sensor unit 104A may sense a motion as any of an exerted pressure, rotation, tilt, push, pull, swipe, drag, twist, and the like. Additionally or alternatively, sensor unit 104A may sense a discrete state or states. Sensor unit 104A includes one or more of: a pressure sensor 104B, an optical sensor 104C (e.g. camera), an acoustic sensor 104D (e.g. ultrasound), a touch sensor 104E (e.g. such as may be integrated with a touchpad), a micro-switch 104F, an opto-switch 104H, and an inertial measuring unit (IMU) 104G. Pressure sensor 104B may be coupled to one or more mechanical components (not shown), such as springs, levers, hinges, and the like that respond to a vertical, horizontal, diagonal, or rotational pressure exerted by the foot, toes, heel, leg, knee, or hip of the user. Optical sensor 104C is operative to capture one or more images, such as of the lower body of the user. Acoustic sensor 104D is operative to sense distance via ultrasonic waves. Touch sensor 104E is operative to detect physical contact (e.g. via changes in capacitance). Micro-switch 104F is operative to detect a discrete state. For instance, opto-switch 104H is operative to detect a discrete state by actuation via the interruption of an optical beam. IMU 104G is operative to perform real-time spatial tracking of translational and rotational motion, and includes one or more micro-electrical-mechanical systems (MEMs), such as 3D accelerometer 104I, a compass (magnetometer) 104J, and a 3D gyroscope 104K. Function switch 104 additionally includes a transmitter 104L. Sensor unit 104A and transmitter 104L are electrically coupled via a bus 104M. In some embodiments, function switch 104 includes one or more processors (not shown).

Function switch 104 provides data sensed by sensor 104A unit to processor 118A of computer 118 (FIG. 1B) via transmitter 104K and transceiver 118B, respectively. In some embodiments, function switch 104 senses continuous motion (e.g. lower-body motion). For example, function switch may be implemented with a camera that provides video data to processor 118A for analysis. As another example, function switch 104 is implemented with an IMU that provides direct motion data as acceleration and angular velocity to processor 118A. In some embodiments, function switch 104 senses discrete states of a foot-operated device providing a single maneuverable mechanical interfacing component. For example, for a function switch implemented as a foot-operated device with a footrest presenting a single point of contact with the surgeon, if the surgeon presses the footrest forward, the function switch will report a first state, and if the surgeon rotates the footrest to the right, the function switch will report a second state, and so on. If the function switch is in a resting state, the function switch will report a resting or neutral state. In an alternative implementation of this example, the function switch can report a rotation state and a tilt state, and the processor will determine the combined state (e.g. rotated and not tilted, tilted and not rotated, not tilted and not rotated, etc.).

The multiple available system functions are stored in memory 118D. In the motion-based implementation, multiple predefined lower body motion sequences are stored in association with the multiple system functions. In the discrete state implementation, multiple sequences, each including at least one discrete state for function switch 104, are stored in association with the multiple system functions. On receiving an indication from function switch 104 of a lower body motion by surgeon 120 (either as a lower-body motion or as a discrete state), processor 118A accesses the association stored in memory 118D to identify the corresponding system function.

Figure 1D:
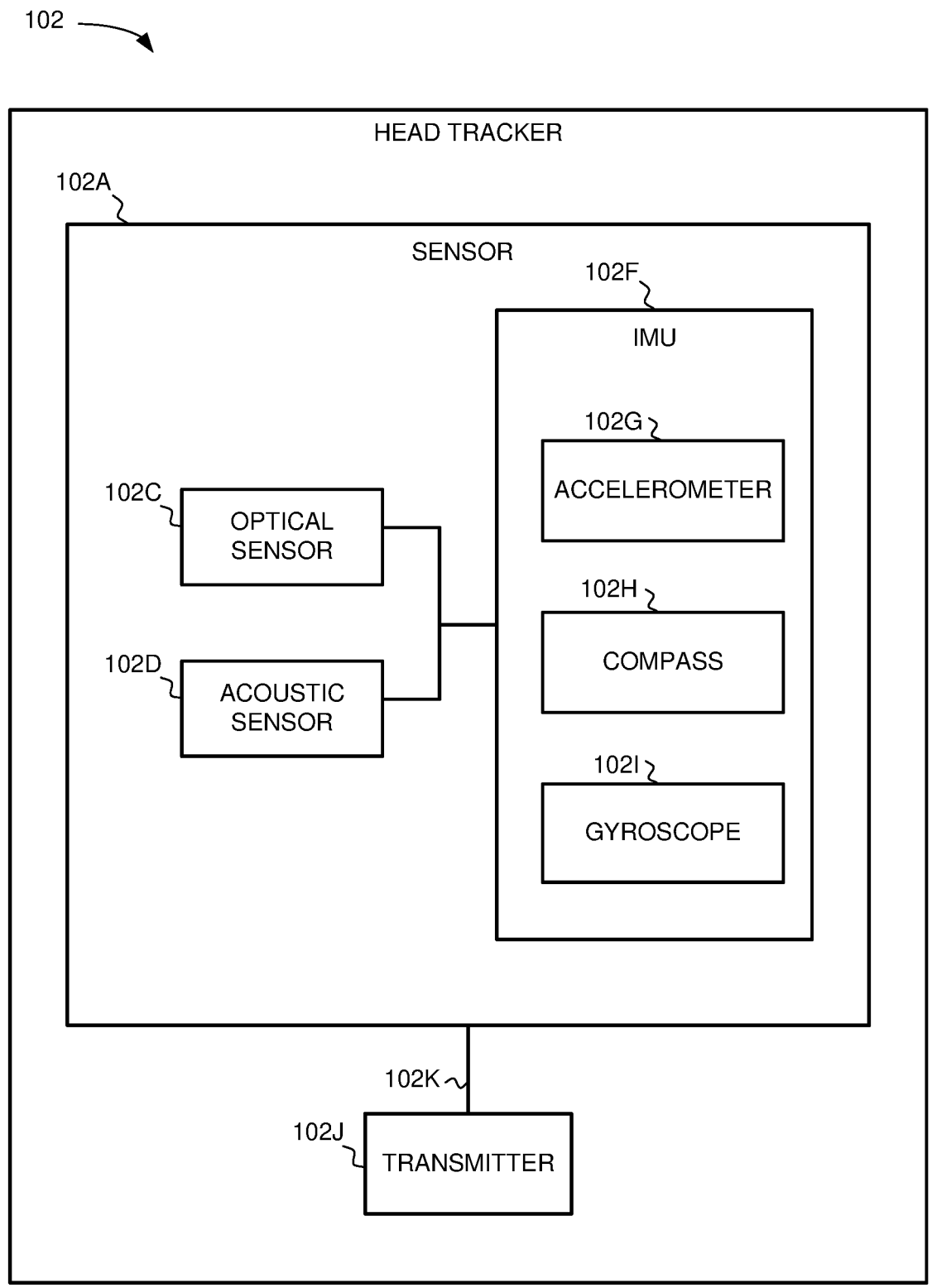

Referring to FIG. 1D, a schematic block diagram of head tracker 102 of FIG. 1A is shown. Head tracker 102 may be any head tracker as is known in the art. FIG. 1D shows an exemplary implementation for head tracker 102. FIG. 1D is not intended to limit the invention to the specific components shown and head tracker 102 may include additional or fewer components than shown in FIG. 1D Similarly, software modules may replace hardware components, and vice versa, where applicable. Head tracker 102 may be implemented based on a tracking unit that is integrated within HMD 103 (with or without additional tracking units), or based on one or more independent tracking units, or a combination thereof. In some embodiments, head tracker 102 is implemented as a standalone system and includes a processor (not shown) for analyzing the tracking data. In other embodiments, head tracker 102 reports any detected tracking data to processor 118A of computer 118. In some embodiments, head tracker 102 is implemented as a wearable device, for example, when integrated with HMD 103. In some embodiments, head tracker 102 is implemented as one or more external sensors, such as a camera or other external sensors that track the head of the surgeon. In some embodiments, head tracker 102 is implemented using a combination of wearable and external sensors.

Head tracker 102 includes at least one sensor unit 102A for sensing any of a position, orientation, and/or motion by the head of the user and a transmitter 102J. Sensor unit 102A and transmitter 102J are coupled via a bus 102K. Sensor unit 102A includes one or more of an optical sensor 102C, an acoustic sensor 102D, and an inertial measuring unit (IMU) 102F. Optical sensor 102C can include one or more cameras that capture markers such as reflective markers or LEDs. IMU 102F includes one or more micro-electrical-mechanical systems (MEMs), such as a 3D accelerometer 102G, a compass (magnetometer) 102H, and a gyroscope 102I for sensing motion. Head tracker 102 provides position and orientation data and/or motion data sensed by at least one sensor 102A to processor 118A of computer 118 (FIG. 1B) via transmitter 102J and transceiver 118B, respectively.

Processor 118A of computer 118 receives data from function switch 104 and applies the data to determine a function for controlling system 100. Processor 118A additionally receives tracking data from head tracker 102, and subsequently applies the head motions (e.g. gestures) to control the determined function of system 100. For example, surgeon 120 may select to enable the focus function by operating function switch 104 with the foot and proceed to adjust the focus settings for camera system 112 using head motions tracked by head tracker 102. In some embodiments, the result of controlling the function manifests in the image that is displayed to the surgeon, e.g. via HMD 103. For example, when the surgeon adjusts the focus setting function for camera system 112 using head motions, the surgeon sees the result of the focus adjustment in the live video acquired by camera system 112 via HMD 103. As another example, when the surgeon uses head motions to adjust other system functions, such as the XY position of camera system 112, illumination settings, image processing settings, scrolling within preoperative images and patient files, operating a menu, or changing an overlay superimposed on the live video stream, the results of controlling these functions manifest as changes in the image that is displayed to the surgeon. In some of these embodiments, the result of controlling the function manifests in the live video from the camera system (e.g. video acquired by the cameras and/or video generated from other sensors in the camera system, such as an iOCT scanning head). In some embodiments, the result of controlling the system function can manifest in the video that is presented to the surgeon also in procedures or in systems without a camera system, such as in VGS procedures or VGS systems.

Processor 118A of computer 118 provides a live video stream of images captured by camera system 112 to HMD 103 for viewing by surgeon 120. In some embodiments, processor 118A includes a GPU for real time processing of the live video stream. In some embodiments, processor 118A includes embedded hardware, field programmable gate array (FPGU), application specific integrated circuit (ASIC), and the like for real time processing of the live video stream. Additionally or alternatively, processor 118A retrieves one or more images, such as preoperative images, data files, guidance information, and the like from memory 118D for displaying via HMD 103. In some implementations, images may be streamed or downloaded from a remote server, such as a cloud based server.

In some embodiments, processor 118A can render pre-acquired imaging data and provide a live stream of the rendered images to HMD 103. For example, in a VGS procedure a model of a body part generated by segmentation from CT or MRI imageries may be stored in memory and rendered on HMD 103 in real-time for viewing by surgeon 120 using conventional techniques. In other embodiments, the images transmitted to HMD 103 are acquired from an external device, such as an endoscope. System 100 may be used for VGS (without camera system 112) at one stage of a procedure, and for microsurgery (with camera system 112) at a later stage. Processor 118A of computer 118 determines which images to stream to surgeon 120 and their format (size, focus, zoom, orientation settings, etc.) based on the current system mode, as well as one or more inputs received from the surgeon via a user interface.

Surgeon 120 wears HMD 103 to view a magnified video of a surgical field 124 while performing a surgical procedure on a patient 122. Camera system 112 acquires a stream of images of surgical field 124, corresponding to surgical procedure performed on patient 122. Computer 118 receives and processes the stream of images acquired by camera system 112 and transmits the processed images via the transceivers to HMD 103 for viewing by surgeon 120. Additionally, surgeon 120 operates function switch 104 to enable the control over one of the multiple functions available for controlling system settings and parameters for system 100, such as camera, illumination, and display settings. In some embodiments, the function enabled by surgeon 120 via function switch 104 is indicated via HMD 103, such as by displaying an overlay superimposed with the live image, presenting the name of the enabled function. After enabling the function via function switch 104, surgeon 120 controls parameters for the enabled function by performing an action that does not require use of the hands, such as via head motions detectable by head tracker 102.

Function switch 104 transmits data to processor 118A for enabling one or more of the available system functions in accordance with any of the embodiments described herein. Thus, the data may include continuously sensed lower-body motion of surgeon 120 and/or continuous indications regarding the current state of the function switch operated by the foot of surgeon 120.

For example, when function switch 104 is implemented with a rotatable and tiltable footrest having multiple discrete states detectable with one or more micro-switches, tilting the footrest forward triggers a first micro-switch of sensor unit 104A to report the forward tilt state to processor 118A of computer 118 via transmitter 104K and transceiver 118B. Processor 118A determines that the forward tilt state of function switch 104 corresponds to an iOCT function, and enables this function accordingly. Once enabled, surgeon 120 controls aspects of the iOCT control function using head motions tracked by head tracker 102, such as by maneuvering the region in the surgical field that is scanned by the iOCT image. Similarly, tilting the footrest backwards triggers another micro-switch of sensor unit 104A to report the backward tilt state to processor 118A. Processor 118A determines that the backward tilt state of function switch corresponds to the pOCT function, which is enabled accordingly. Once enabled, surgeon 120 controls aspects of the pOCT function using head motions tracked by head tracker 102. By maneuvering function switch 104 via the single point of interface using combinations (e.g. sequences) of tilt, rotation, press, push, tap motions, and the like, surgeon 120 can enable a wide variety of functions for controlling system 100.

As another example, when function switch 104 is implemented using a sensor, such as an IMU, for detecting motion of a footrest, turning the footrest clockwise causes sensor 104A to transmit the clockwise motion data to processor 118A via transmitter 104K and transceiver 118B. Processor 118A analyzes the data to identify the clockwise turn and matches this to the library of predefined motion sequences stored in memory 118D. Processor 118A determines that the clockwise turn corresponds to the Zoom control function, and enables this accordingly. Once enabled, surgeon 120 controls aspects of the Zoom function using head gestures that are tracked by head tracker 102. Similarly, turning the footrest counter-clockwise causes sensor 104A to transmit the counter-clockwise motion data to processor 118A. Processor 118A analyzes the data to identify the counter-clockwise turn and matches this to the library of predefined motion sequences. Processor 118A determines that the counterclockwise turn corresponds to the Illumination control function and enables the Illumination. Once enabled, surgeon 120 controls aspects of the Illumination using head motions tracked by head tracker 102.

It is to be understood that these are but exemplary implementations that do not limit the invention, which may be implemented via any of the embodiments described herein. For example, while function switch 104 is illustrated as a foot-enabled device positioned on the floor with a moveable footrest, other implementations are possible, such as via a wearable device, a chair-mounted device, a touchpad, and the like.

In some embodiments, function switch 104 senses motion via a single point of interface for surgeon 120. For example, a footrest element provided with function switch 104 may include a pivot that may be tilted forwards and backwards, and rotated clockwise and counterclockwise, allowing surgeon to select from multiple functions without lifting the foot from the footrest, and eliminating the need for numerous buttons. Consequently, function switch 104 is simpler to operate, and allows surgeon 120 to wear shoes during surgery.

In some embodiments, more than one control modality may be used. In some embodiments most of the system functions are controlled with head motions and the function switch as described herein, but some system functions may be directly controlled by a separate control modality. For example a separate joystick may control the XY motors for the camera, while other functions are controlled using head motions and the function switch. As another example, one or more dedicated buttons may be provided with the function switch, such as a button for saving a snapshot of the live video and a button for toggling between two system modes. Dedicated buttons may be implemented either as physical buttons or as virtual buttons (e.g. when the function switch is implemented with a wearable tracker or with a touchpad).

Reference is now made to FIGS. 2A-2G which, taken together with FIGS. 1A-1D, illustrate another exemplary user interface, generally referenced 200, for enabling and controlling functions of a surgical system, constructed and operative in accordance with another embodiment of the disclosed technique. User interface 200 may include an optional output interface referred to herein as a function slider 202 for displaying control options to surgeon 120, such as via HMD 103. User interface 200 additionally includes an input interface via function switch 204, corresponding to function switch 104 (FIGS. 1A and 1C). Function switch 204 is configured as described above, either to sense lower body motions of surgeon 120, or to sense discrete states as a result of being maneuvered by surgeon 120. In the exemplary embodiment shown, surgeon 120 maneuvers function switch 204 with his foot 206, however this is not intended to be limiting. Function slider 202 displays various system functions to surgeon 120 for controlling system 100 via HMD 103, such as "Illumin" 208 for controlling illumination settings, "Focus" 210 for controlling the focus, and "Zoom" 212 for controlling the zoom of the cameras provided with system 100.

Surgeon 120 maneuvers function switch 204, such as by rotating a footrest provided therewith with the foot, to invoke one or more of the optional function sliders, each presenting multiple control functions. Surgeon 120 may invoke the sliders without performing a dedicated invoking action, i.e. just by rotating function switch 204 with a clockwise or counterclockwise rotation of foot 206. Alternatively, surgeon 120 may invoke the function sliders with a dedicated action, such as tilting and releasing function switch 204 with foot 206. Processor 118A receives an indication from function switch 204 that surgeon 120 has initiated the process of function enablement. When a function slider is presented, initiating the process of function enablement is equivalent to invoking the function slider. Processor 118A displays the function slider via HMD 103. In some embodiments, the function slider is invoked in response to a movement that exceeds a threshold to prevent small movements from invoking the function slider. Optionally, if a function slider is invoked unintentionally, processor 118A resets the process of function enablement and removes the function slider from the display if there is no action detected by either the head tracker or the function switch for a predefined time period, such as 2 seconds. In some embodiments, surgeon 120 invokes a function slider by quickly moving and releasing the footrest. In response, processor 118A displays the invoked function slider and highlights the default function. In some embodiments, surgeon 120 invokes a function slider by shifting (i.e., tilting, or pressing, or tilting and pressing) the footrest directly to the desired state, in which case the appropriate function is highlighted upon invoking the slider.

Figure 2A:
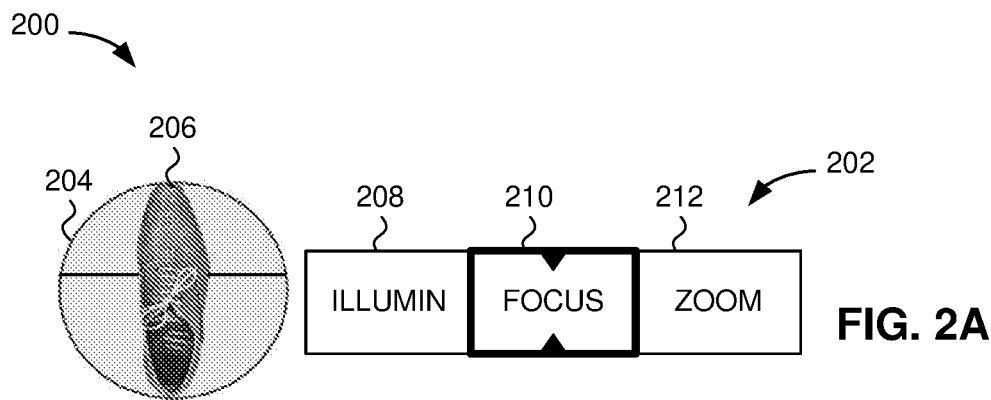
FIGS. 2A-2G, taken together with FIGS. 1A-1D, illustrate another exemplary user interface for enabling and controlling functions of a surgical system, constructed and operative in accordance with another embodiment of the disclosed technique.
Figure 2B:
Figure 2C:

After invoking function slider 202, surgeon 120 can maneuver the footrest of function switch 204 to comfortably scroll through the list of system functions displayed in function slider 202 and highlight the function to be controlled (e.g. if the desired function isn't already highlighted). Once the function has been highlighted, surgeon 120 can control the highlighted function using head motions tracked by head tracker 102 (FIG. 1D). In the exemplary embodiment of FIGS. 2A-2C, a single function slider 202 is shown presenting three system functions: Illumination 208, Focus 210, and Zoom 212. The selected function highlighted on function slider 202 corresponds to the orientation of the footrest of function switch 204 as surgeon 120 maneuvers it with the foot 206. In FIGS. 2A-2C, a line is shown for clarity to indicate that the footrest rotates with the foot of surgeon 120. It is to be appreciated that, according to this embodiment, the footrest moves with the foot of surgeon 120 in the other drawings, even where no line is shown.

It is to be noted that the sliders described herein alleviate the need for the surgeon to remember the various motions needed to select the different functions. This may be advantageous when the user is not yet familiar with the system or when the function layout is user-configurable. An exemplary implementation for manipulating function switch 204 with the foot to control system 100 is now described. In the examples given below, it is to be understood that foot motions by surgeon 120 are detected by sensor 104A (FIG. 1C) of function switch 104 and provided to processor 118A (FIG. 1B) of computer 118, as described above. Processor 118A analyzes the detected foot motions to determine a function for enablement and displays a corresponding function slider 202 to surgeon 120 that presents the selected function and assists the surgeon to adjust the selection.

While the description that follows relates to a foot switch having a sensor to sense motion, it is to be understood that a similar user interface may be implemented with a foot switch sensing discrete states. In this case, as the surgeon moves the footrest of the function switch with the foot, the function switch reports an indication of the current state. The indication may relate to one or more degrees of freedom, such as rotation state in combination with a tilt state, or such as a separate flag for each discrete state. Moreover, while the description that follows describes navigating a function slider by rotating the foot, the function switch may be configured to allow navigating the function slider using any suitable motion other than rotating, such as tilting or pressing, and the like. The function switch may allow the surgeon to configure which motion enables different features according to personal preferences. Similarly, while the function slider(s) are shown in a horizontal orientation, the sliders may be oriented in any suitable manner, such as vertically, as a dial, and may be set according to the preferences of surgeon 120.

Referring to FIG. 2A, function slider 202 is invoked and displayed to surgeon 120 via HMD 103. When surgeon 120 holds foot 206 straight, processor 118A of computer 118 receives an indication regarding the straight orientation from function switch 204, and determines that the position corresponds to the default function "Focus" 210, presented in the middle of function slider 202 (e.g. the default function is the focus function, represented by "Focus" 210 in the function slider). Processor 118A of computer 118 highlights "Focus" 210 with indicative arrows.

Referring to FIG. 2B, surgeon 120 turns foot 206 to the left in a counterclockwise rotation. Processor 118A receives an indication of the counterclockwise rotation from function switch 204, either as a discrete state (or states, e.g. left rotation state and zero tilt state) or as a motion. Processor 118A determines that the counterclockwise rotation (or state) corresponds to the "Illumin" function 208, presented on the left side of function slider 202 and highlights it with indicative arrows.

Referring to FIG. 2C, surgeon 120 turns foot 206 to the right in a clockwise rotation. Processor 118A receives an indication of the rightward rotation, either as a sensed motion or as an indication of a discrete state. Processor 118A determines that the corresponding function is "Zoom" 212, presented on the right of function slider 202, and highlights the display accordingly, with indicative arrows.

Figure 2D:
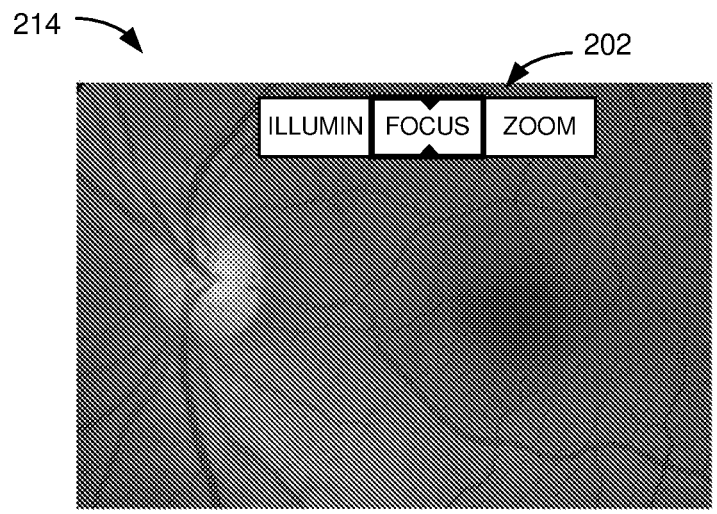

Referring to FIG. 2D, processor 118A of computer 118 displays function slider 202 overlaid on an image 214 viewed by surgeon 120 via HMD 103. Surgeon 120 may navigate the options presented on function slider 202 using intuitive, natural motions to highlight and enable different control functions for system 100, while viewing the live image stream 214 acquired via camera system 112.

Figure 2E:
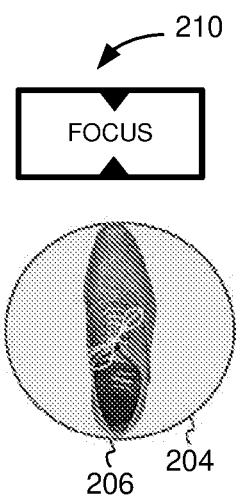
Figure 2F:
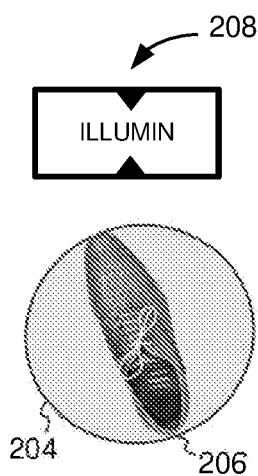
Figure 2G:
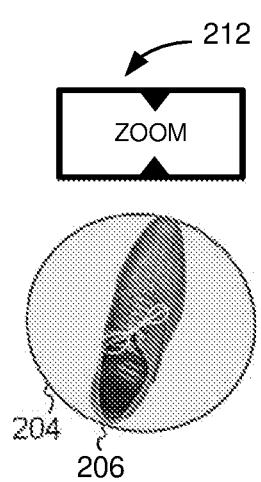

Alternatively, referring to FIGS. 2E-2G, in some embodiments, function slider 202 only displays the currently selected function instead of all the available options. Turning to FIG. 2E, processor 118A of computer 118 displays just "Focus" 210 via HMD 103 when the orientation of foot 206 on function switch 204 is straight forwards. Turning to FIG. 2F, processor 118A of computer 118 displays just "Illumin" 208 via HMD 103 when the orientation of foot 206 on function switch 204 is leftwards. Turning to FIG. 2G, processor 118A of computer 118 displays just "Zoom" 212 via HMD 103 when the orientation of foot 206 on function switch 204 is rightwards.

Function switch 204 may be used with systems other than HMD-based systems. For example, function slider 202 may be displayed on a conventional, non-wearable display. It is to be noted that the function switch is particularly beneficial when used in conjunction with a system which tracks the user's head movements, such as system 100 of FIG. 1A, for applications where the user's hands are occupied, such as in surgery. In such applications, system functions can be controlled via tracked head motions, freeing the surgeon's hands. Head tracking may be implemented by a head tracker 102 integrated with an HMD such as HMD 103. Alternatively, head tracking may be implemented without an HMD, for example, by implementing head tracker 102 using a camera capturing the head movements of surgeon 120, or as a head wearable tracking device (e.g. without a display), and the like.

In some embodiments, the functions displayed to surgeon 120 may be organized in a long list (e.g. a single function slider) that includes all the system functions, or alternatively may be organized in several separate lists (e.g. multiple function sliders), and surgeon 120 may easily invoke the desired function slider using the same function switch 204. In addition, a default function slider may list the most relevant system functions based on the current system mode (i.e. the functions listed in the default slider may change according to the current system mode). When using separate sliders, a single tap may be used for invoking a default slider (e.g. when the function switch is implemented with a wearable tracker or with a touchpad), a double tap for a secondary slider, and in general any number of taps for any number of sliders. Alternatively, sliders may be invoked by tilting the foot in different directions (e.g. with the rotatable footrest or with tracking) and/or for different periods of time (e.g. a short tilt, without holding the footrest tilted, to invoke one slider, and long tilt, without holding, to invoke a second slider).

Reference is now made to FIGS. 2H-2K which, taken together with FIGS. 1A-1D, illustrate another exemplary user interface for enabling and controlling functions of a surgical system, constructed and operative in accordance with a further embodiment of the disclosed technique. The user interface of FIGS. 2H-2K is substantially similar to that described above with respect to FIGS. 2A-2C with the notable difference that multiple function sliders, i.e. top function slider 220 and bottom function slider 222 are overlaid on a live image viewed by surgeon 120 via HMD 103, (i.e. as opposed to a single function slider). Two function sliders are shown for exemplary purposes only, and three or more function sliders may be similarly presented.

In some embodiments, a slider may be invoked without a single default function being highlight. For example, the surgeon may invoke a slider with a slight foot movement and then return the function switch to a resting state to highlight two functions. Subsequently the surgeon can operate the foot rest until a single function is highlighted (e.g. selected) and enabled, and continue to control the selected function via head gestures. In some embodiments, a slider may be invoked with a single default function being highlight. For example the surgeon may tilt the function switch without releasing to highlight a single function. Subsequently the surgeon can immediately continue to control the selected function via head gestures. The display of the sliders is of course optional. The processor determines the enabled function based on the sequence of motions (or discrete states), regardless of the display of the sliders.

Function switch 204 is maneuvered by surgeon 120 to invoke and operate function sliders 220 and 222, displayed via HMD 103. Once function sliders 220 and 222 are invoked, at any given moment, two functions are highlighted, one per slider. Surgeon 120 may scroll through the functions by rotating foot 206 on function switch 204. Surgeon 120 may press forward (forward tilt) with the front of foot 206 to leave only the function of top function slider 220 highlighted or press with the heel of foot 206 (backward tilt, FIG. 2J) to leave only the function of lower function slider 222 highlighted. Processor 118A of computer 118 receives a signal indicating the motion of surgeon 120 as described above (i.e. either as a continuous motion or a discrete state) and highlights the function (or functions) on HMD 103 accordingly. Once only one function is highlighted, the surgeon may start controlling the highlighted function using head motions.

Figure 2H:
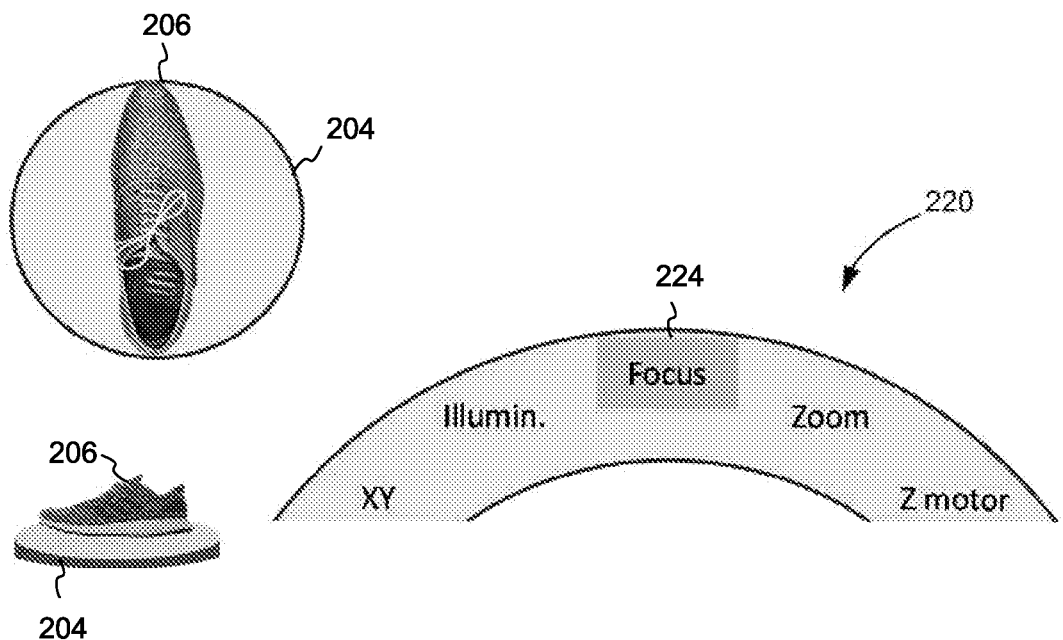
FIGS. 2H-2K, taken together with FIGS. 1A-1D, illustrate another exemplary user interface for enabling and controlling functions of a surgical system, constructed and operative in accordance with a further embodiment of the disclosed technique.
Figure 2H:
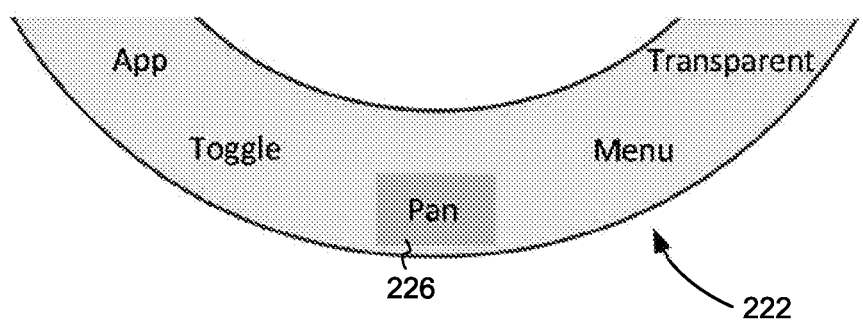
Figure 2I:
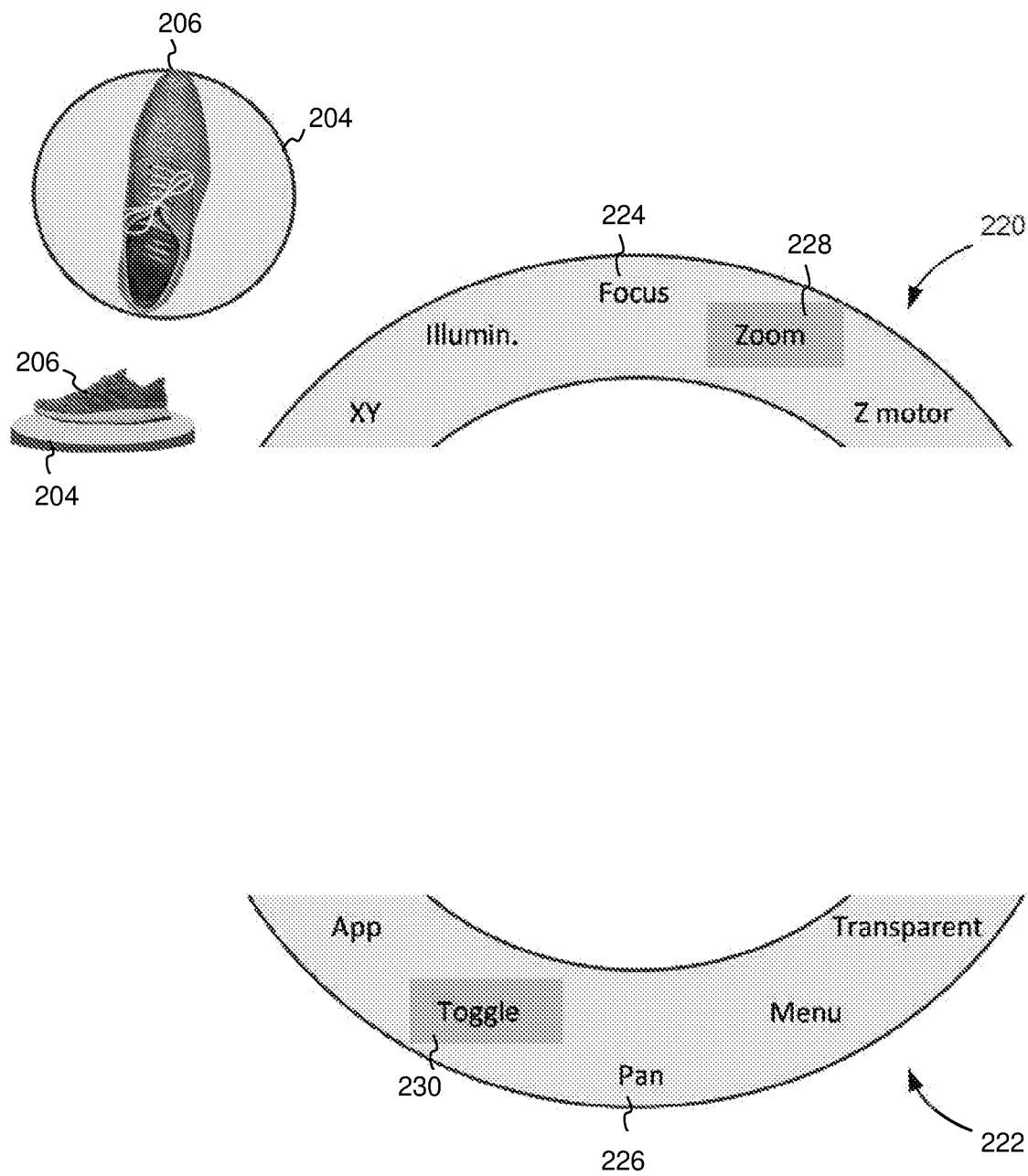
Figure 2J:
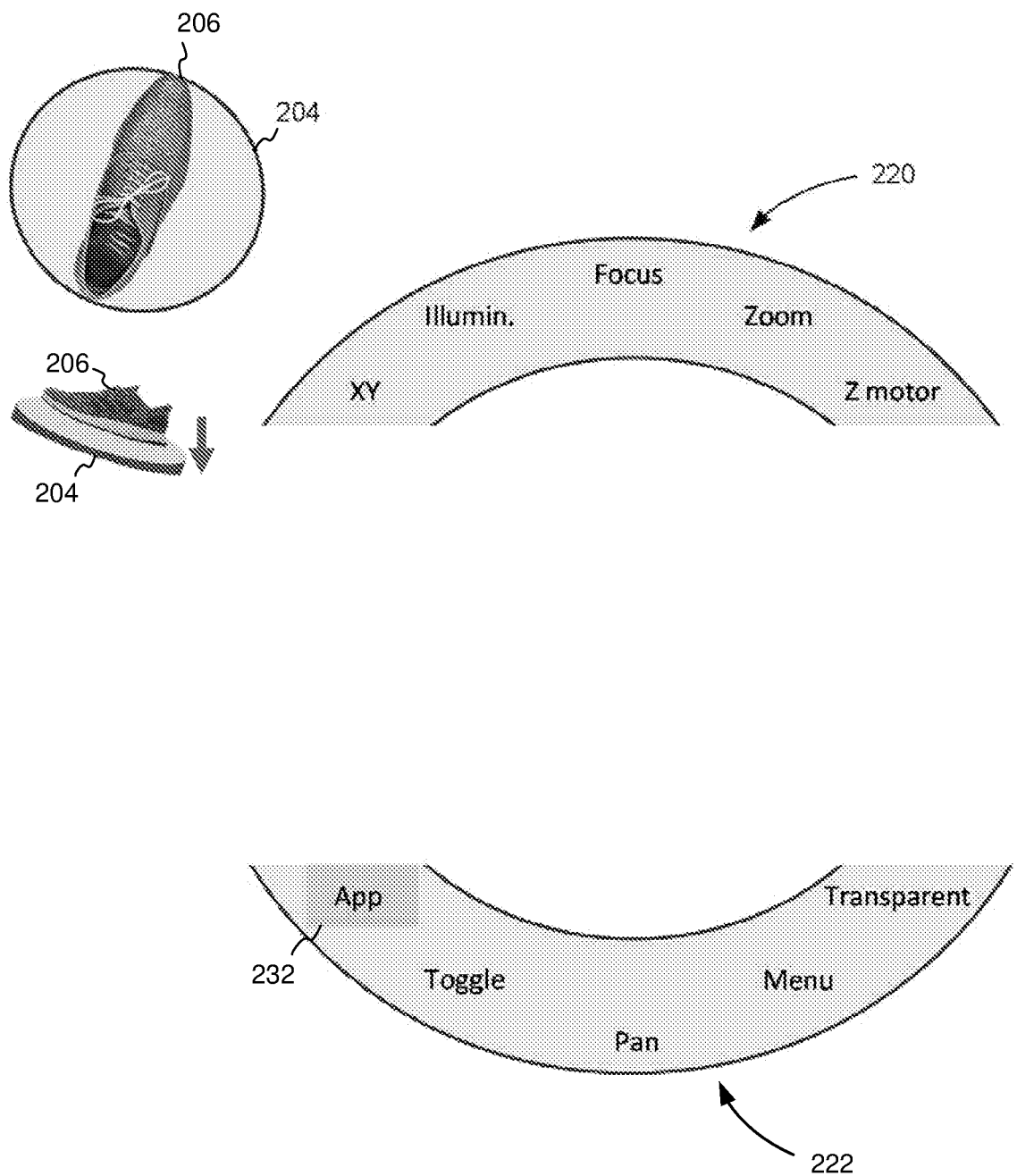

Processor 118A of computer 118 associates function slider 220 (top) with the orientation of the front of function switch 204, such as may be manipulated by the front of foot 206. Processor 118A of computer 118 associates function slider 222 (bottom) with the orientation of the rear of function switch 204, such as may be manipulated by the heel of foot 206. For each of FIGS. 2H-2J, foot 206 is shown from a top perspective to indicate rotation and a side perspective to indicate tilt. Referring to FIGS. 2H-2J, a sequence of actions by foot 206 is shown for controlling function sliders 220 and 222. In FIG. 2H, once the function sliders are invoked, surgeon 120 orients foot 206 straight forwards and flat (no tilt). Processor 118A of computer 118 receives a signal indicating the straight forwards and flat position from function switch 204. Processor 118A highlights the display of the default function, "Focus" 224 of upper function slider 220, corresponding to the straight forwards orientation of the front of foot 206. Similarly, processor 118A highlights the display of the default function "Pan" 226 of lower slider 222, corresponding to the straight orientation of the heel of foot 206.

In FIG. 2I, surgeon 120 rotates foot 206 on in a clockwise direction. Processor 118A receives a signal from function switch 204 indicating the clockwise rotation. In response, processor 118A highlights functions other than the default functions. For example, processor 118A highlights the display of "Zoom" 228 on upper function slider 220, positioned to the right of "Focus" 224 and corresponding to the rightwards orientation of foot 206 on function switch 204. Similarly, processor 118A highlights the display of "Toggle" 230 on lower function slider 222, positioned to the left of "Pan" 226 and corresponding to the leftwards orientation of the back of foot 206. If surgeon 120 further rotates foot 206 clockwise on (i.e. top of foot 206 is rotated rightwards, and bottom of foot 206 is rotated leftwards), function switch 204 provides an indication of this motion to processor 118A, which highlights the displays of two other functions, e.g. "Z motor" to the right of "Zoom" 228 on upper slider 220 and "App" to the left of "Toggle" 230 on lower function slider 222.

To select the function highlighted on lower function slider 222, surgeon 120 presses with the heel of foot 206. Processor 118A receives a signal indicating the heel press from function switch 204 and leaves only the respective function highlighted. Similarly, to select the function highlighted on upper function slider 220, surgeon 120 presses with the front of foot 206. Processor 118A receives a signal indicating the front foot press from function switch 204 and leaves only the respective function highlighted. Referring to FIG. 2J, pressing the heel of foot 206 down selects the App function 232 of function slider 222 that was previously highlighted on slider 222.

Figure 2K:
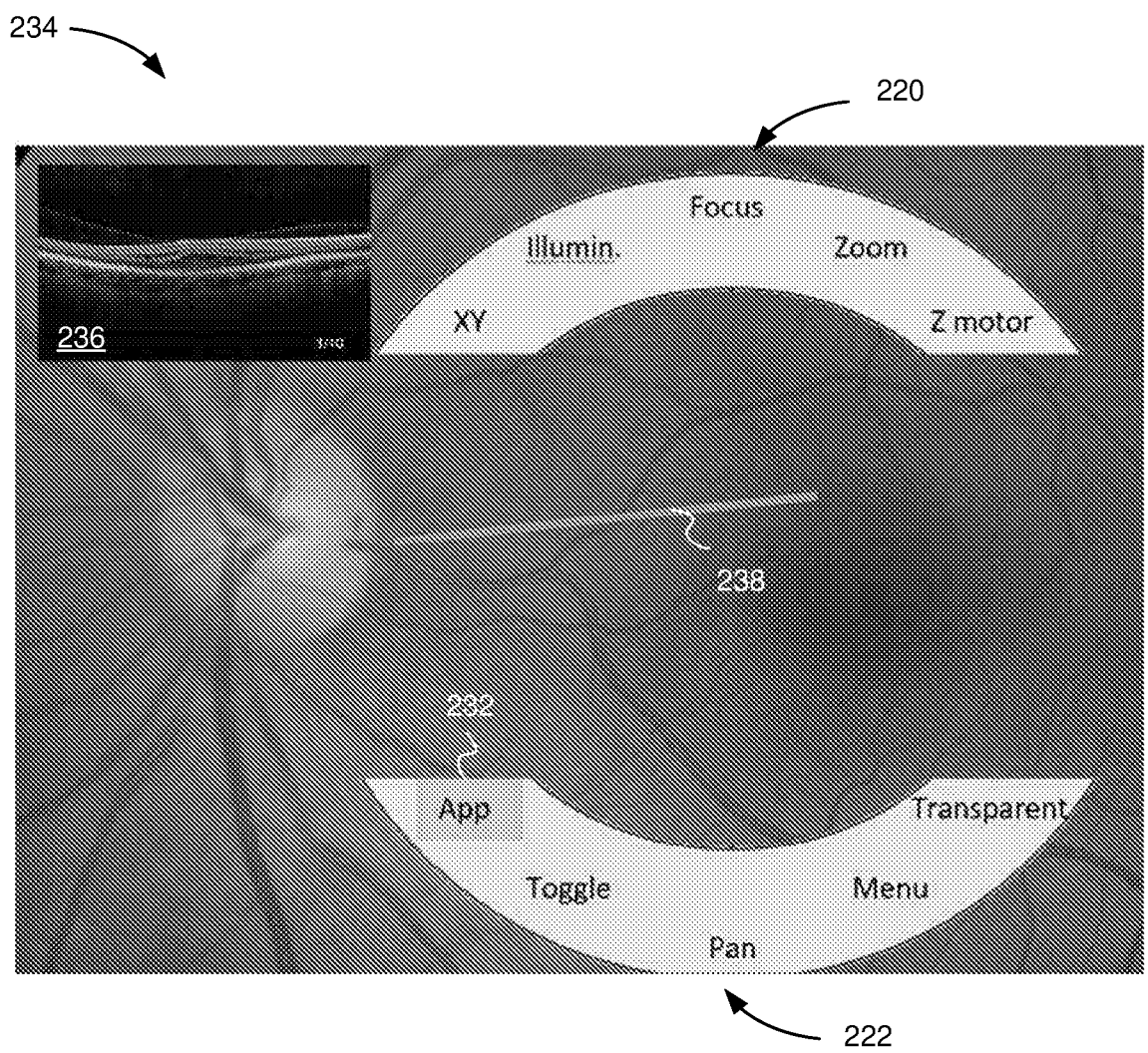

Referring to FIG. 2K, function sliders 220 (top) and 222 (bottom) are shown overlaid on a live image 234 displayed via HMD 103. Upper function slider 220 presents five control options, from left to right: XY (i.e. XY motors), Ilium (i.e. Illumination), Focus, Zoom, and Z motor. Lower function slider 222 presents five additional control options, from left to right: App 232 (i.e. Application operation), Toggle (i.e. Toggle system mode), Pan, Menu, and Transparent (i.e. to open the HMD shutter). The size of function sliders 220 and 222 has been exaggerated for illustrative purposes. In the example of FIG. 2K, an application called pOCT is already activated. This application allows the user to view preoperative OCT scans along with a line indicating the location, on the retina, that corresponds to the scan location. This is illustrated by the B-scan 236 displayed in PIP and a line 238 indicating the corresponding location of the B-scan 236, overlaid on live image 234. Selecting "App" allows the user to scroll through the various OCT B-scans by adjusting the corresponding locations of line 238 with head motions. The pOCT is an example of one application that may be controlled using head motions when the "App" function 232 is enabled, shown highlighted. Other applications may similarly be controlled when "App" 232 is selected, such as the Teaching app, the Toric Alignment app, the Intraoperative OCT app, and many others.

Referring back to FIGS. 1A-1D, alternatively or in addition to displaying the function sliders (e.g. sliders 202, 220 or 222) and highlighting the current function via HMD 103, or stand-alone display, processor 118A may provide surgeon 120 with additional feedback, such as a vibration by a vibration motor (not shown), for instance a piezoelectric motor configured with the footrest of the function switch. As another example, processor 118A may emit a sound or pronounce the name of the selected function via a speaker (not shown). Processor 118A may emit the beep when surgeon 120 changes the selected function while scrolling. Function switch 104 may allow for continuous scrolling, or discrete scrolling. In the latter case, function switch 104 can be provided with tactile bumps (e.g. actual or virtual bumps, for instance virtual bumps implemented with a vibration motor) such that surgeon 120 feels discrete angular steps when rotating or tilting the footrest. The rotatable footrest may generate a tactile feedback when surgeon 120 rotates between various functions (e.g. with "bumps" positioned for every 5 degrees of rotation). In some embodiments the step size, along with the additional feedback, may be reconfigured if different surgeons prefer different angular differences between adjacent functions (or different distances when scrolling is performed for instance by moving the foot along a straight line over a touchpad). The additional feedback may assist surgeon 120 to scroll through different options while keeping his eyes on the surgical field, and without having to avert his gaze to the function slider displayed via HMD 103. At first, some surgeons may prefer having the available functions displayed. However, once a surgeon becomes accustomed to the various options offered by system 100 described herein, displaying all the options each time may be unnecessary and even distracting. The learning curve may be different for each user and can allow for customization. In some embodiments, the function slider is always displayed, even if it is just for seeing the function switching in the background without gazing towards it. However, after learning to rely on the additional feedback, the user may choose to disable the displaying of the function slider.

In some embodiments, processor 118A does not display the function sliders to surgeon 120. For example, in FIGS. 2A-2G, function switch 204 can rotate all-the-way left or right and tilt all-the-way forward or backward, so no additional feedback is necessary. Displaying the function slider or not may be user configurable. In some embodiments, when the function slider is not displayed, another indication is provided by the system that indicates that the process of function enablement has been initiated. This can be provided for user awareness, for instance if the user accidently initiated the process. The indication can be provided via the HMD or by any other means.

Surgeon 120 may control an enabled function with one or more head motions (e.g. gestures) tracked by head tracker 102. Head motions may be considered in process either while the head is moving, or for a predetermined time period after head movement has ceased. This is to allow for small pauses in head motions, e.g. in order to evaluate if the function requires further adjustments.

The following are several examples of functions and their control via head motions:
Focus:
   Up-down head motion: focus in and focus out.
   Left head motion: toggle auto-focus (on/off).
   Right head motion: open auto-focus menu.
Zoom:
   Up-down head motion: zoom in and zoom out.
   Left head motion: toggle auto-zoom (on/off).
   Right head motion: open auto-zoom menu.
Illumination:
   Up-down head motion: increase/decrease illumination.
   Left head motion: toggle dim illumination (dim on/dim off).
   Right head motion: toggle illumination (on/off).
XY motors:
   Up-down head motion: move Y.
   Left-right head motion: move X.
Z motor:
   Up-down head motion: move Z.
Robotic arm:
   Alternatively to the XY and Z motors, various head motions may control a 6-DOF robotic arm (e.g. in a neurosurgery system)
   Several types of enslavement to head motions may be pre-defined, such as:
     Changing only the distance of the camera head unit from the surgical field, without changing the viewing direction.
     Changing the viewing direction of the camera head unit such that the cameras' center of FOV is locked to a point in the surgical field.
     XY motion without changing the distance and/or the viewing direction.
     Slaving both position and orientation of the camera head unit to head motions.
   Each of the above types (and optionally other types) may be considered a unique function.
Panning
   Similar to XY motors, but scrolling an ROI within an entire frame (i.e. when zooming in the entire frame to magnify the displayed image).

In some embodiments, surgeon 120 may control a menu as a function controllable by performing head motions. Processor 118A displays the menu via HMD 103. Surgeon 120 navigates the menu by performing head motions detected by head tracker 102, and enabled by function switch 104. In these embodiments, surgeon 120 scrolls within the menu by performing head motions, as differentiated from scrolling within a function slider with the foot (or chair, etc.). An exemplary list of actions for operating the menu for two of the many possible embodiments of the function switch is listed as follows:

Menu operation in the embodiment of a rotatable footrest
        Enabling the menu: pressing with the heel.
        Operating the menu: head motions.
        Activating a menu item: depressing (stop pressing) the heel.
    Menu operation in the embodiment of a wearable tracker (e.g. wearable on the foot, leg, knee, ankle, hips, waist, and the like)
        Enabling the menu: lifting the heel.
        Operating the menu: head motions.
        Activating a menu item: resting the heel/tapping with the heel.

Following is an exemplary menu that includes sub-menu items for eye surgery applications. It is to be noted that other menus may be implemented for eye surgery or for other fields, such as neurosurgery and the like.

System modes menu
        Anterior;
        Posterior wide lens;
        Posterior flat lens.
    Image enhancements menu ("filters")
        ICG enhancement;
        BBG enhancement;
        Sharpening.
    Applications menu
        Toric alignment;
        Pre-planning;
        Preoperative OCT;
        iOCT;
        Endoscope;
        Teaching.

The menu items that are displayed via HMD 103 may change dynamically and may depend for example on the type of procedure, the stage of the procedure, the system mode, user preferences, and the available Apps, such as Apps licensed by surgeon 120. For instance, once an App is activated by surgeon 120, the menu may include an additional menu item (with a sub-menu) for controlling the App attributes. Surgeon 120 first activates the App by selecting it in the above Apps menu. Surgeon 120 may terminate the App via the dedicated App menu that is added once the App is activated. In another example, if a phaco-vitrectomy device is connected to system 100 and is activated, a menu item (with a sub-menu) may be added to allow the user control over the display of phaco-vitrectomy settings and metrics, and possibly also the control over some settings. In a further example, in cataract procedures, a dedicated guidance overlay menu item may automatically be added once the phaco device metrics streaming is discontinued.

In some embodiments, surgeon 120 scrolls through and operates the menu directly via function switch 104, without performing head motions. In these embodiments, once the menu is invoked, surgeon 120 scrolls within the various menu items and the sub-menus using function switch 104.

The process of selecting, enabling and controlling a function may be terminated at any point, as described below, with respect to FIGS. 1A-1D. Note that when a slider is displayed, terminating the function slider is equivalent to terminating the process of selecting, enabling and controlling a function. When a slider is not displayed the process is terminated in the same way:

Terminating the function slider—by timer
        If a slider is accidently invoked, the slider will automatically disappear if no scrolling is detected by function switch 104, or no controlling head motions are identified by head tracker 102 for a predetermined time period, e.g. 0.5 seconds (time durations are configurable).
    Terminating the function slider after starting to scroll—by timer
        If surgeon 120 changes his or her mind after starting to scroll within the functions of a function slider, and doesn't want to control any function with head motions, the slider will disappear if no scrolling or controlling head motions are identified by any of function switch 104 and head tracker 102 for a predetermine period, e.g. 1 second.
    Terminating the head motions—by timer, by releasing, or e.g. by tapping or tilting.
        In some embodiments, upon completing a head motion to control a function, surgeon 120 may terminate the action actively, e.g. by tapping the foot (e.g. when function switch 104 is implemented as a touchpad or with a tracker), or by tilting or releasing the footrest of function switch 104 (e.g. when the function switch is implemented with a footrest, as shown in FIGS. 3A-3D, described below). For example, when a function is enabled by releasing the footrest (i.e. un-rotated and un-tilted), surgeon 120 may terminate the enablement of a function by a forward tilt and release action by the foot on function switch 104. Surgeon 120 may enable the focus function by performing a forward tilt and release of the footrest of function switch 104. Similarly, surgeon 120 may enable the zoom function by performing a clockwise rotation and release of the footrest of function switch 104. Alternatively, once head motions are initiated and tracked by head tracker 102, surgeon 120 may release the footrest without affecting the enablement. In both cases, the enablement may be terminated with a tilt forward and release of the footrest of function switch 104.
    Alternatively, in some embodiments, termination may be implemented with a timer, for example if no foot or head motions are identified by either of function switch 104 and head tracker 102 for a predetermined period, e.g. 2 seconds, the process is terminated, and the selected function is no longer displayed via HMD 103.
    Alternatively, in some embodiments, in one implementation of a rotatable footrest of function switch 104, enabling a function may require surgeon 120 to continually press or rotate the footrest for the duration of the enablement. Releasing the footrest of function switch 104 terminates the enablement.

In some embodiments, a select group of functions comprise a quick activation that does not require any head motions to be performed by surgeon 120. The number of quick-access functions may vary and may be configured by surgeon 120. Following are several examples of functions that may require quick access:

Toggle to last mode
        This allows to quickly switch between the anterior mode and the posterior wide lens mode, or between the anterior mode and the posterior flat lens mode.
    Application operation (the "App" function)
        The app function allows for special application capabilities.
        For example when used when the pre-planning app is active, selecting the app function momentarily freezes the live image and shows pre-planning overlays on the frozen image. This capability doesn't require any head motions.

Note that the same "App" function may also serve to enable head motions when used together with other apps, for instance:

Enable head motions to scroll within preoperative images (e.g. including the pOCT application with the line overlaid on the live image).

Enable switching between system modes with head motions (see FIG. 5I further below).

Snapshot

For saving a snapshot of the live image at memory 118D.

Video recording (start/stop) stored at memory 118D.

Bookmark

For saving a pointer at memory 118D to a specific moment during the surgery for future reference (in this case the system may prompt the user to name the bookmark, e.g. using voice-to-text).

The quick access feature may be implemented for example by one of the following actions:

Tilting and/or rotating footrest of function switch 104 to highlight a function, and releasing the footrest to activate the highlighted function.

Special tapping of the footrest of function switch 104.

Touching virtual buttons, e.g. with a touchpad (not shown) provided with function switch 104.

Touching physical buttons (not shown) adjacent to function switch 104.

For example when using the turntable implementation, surgeon 120 may achieve quick access by performing the following:

Tilting with heel and then rotating the footrest of function switch 104 in a counterclockwise direction accesses the application button.

Tilting with heel and then rotating the footrest of function switch 104 in a clockwise direction accesses the toggle to last mode function.

During specific stages of a surgical procedure, surgeon 120 may wish to continuously dedicate head motions to a single function, without being required to select the function via function switch 104, as described above. For example, in a neurosurgical procedure, surgeon 120 may wish to control robotic arm 106 holding the camera head 110 using head motions detected by head tracker 102. In another example, during a retinal procedure, surgeon 120 may wish to control the panning action (changing the displayed ROI) or the XY motors using head motions. As a further example, surgeon 120 may continuously control the focus function. In order to do this, the surgeon may instruct system 100 to "lock" a specified function (e.g. lock the enablement of the function). Locking may be implemented, for example, by double tapping the foot on function switch 104 while performing head motions to control a function (e.g. double tapping locks a function and a single tap unlocks it). Surgeon 120 may lock a function via function switch 104 by performing a quick tilt-and-release of the footrest or a release of the footrest if it is already tilted, while head motions are in process. To unlock the function, surgeon 120 may perform an additional quick tilt-and-release. In some embodiments, functions are locked by default once they are selected and surgeon 120 has begun performing head motions. Surgeon 120 unlocks (or terminates) the function enablement by performing a predefined motion, such as a tap or tilt and release.

In some embodiments, system 100 may be configured to ignore some or all inputs from function switch 104 while head motions are in progress. This may be useful to avoid accidentally switching to a new function while surgeon 120 is controlling a selected function. In some cases, surgeon 120 may control system 100 by operating function switch 104 while simultaneously performing head motions tracked by head tracker 102, for example:

To lock a function, e.g. with a double tap or tilt of the foot on function switch 104 while head motions are in process, as described above.

To terminate control via head motions, e.g. with a tap or tilt on function switch 104 while head motions are in process (note that head motions may be considered in process also for a predetermined period of time after the head stopped moving).

Reference is now made to FIGS. 3A-3D which taken together with FIGS. 1A-1D, illustrate an exemplary implementation of a function switch for controlling a surgical system, generally referenced 304, constructed and operative in accordance with another embodiment of the disclosed technique. Function switch 304 senses motion along two degrees of freedom, i.e. tilting (up and down) and rotation (right and left). Function switch 304 includes a footrest 306, a platform 308, and one or more pivots 310. Function switch 304 may additionally include a combination of springs, levers, hinges, and the like. Footrest 306 is mechanically coupled to platform 308 via pivots 310, which allows footrest 306 to tilt and rotate with respect to platform 308.

In some embodiments, footrest 306 is moveable relative to function switch 304. Alternatively, footrest 306 is moveable relative to the floor and the function switch moves together with the footrest. Function switch 304 may include sensors that detect continuous tilt and rotation motion by surgeon 120 on footrest 306. Alternatively, function switch 304 senses multiple discrete states as surgeon 120 maneuvers footrest 306. Function switch 304 may sense multiple states at a given moment, such as a back tilt with the rightwards rotation. The surface of footrest 306 may be covered with rubber to prevent slippage as surgeon 120 rotates the foot on footrest 306, such that footrest 306 rotates with the foot. Additionally or alternatively, footrest 306 may have adjustable stoppers on the sides to accommodate the width of the foot.

One or more sensors (e.g. sensor 104A of FIG. 1C) detect the tilt and rotational angle of footrest 306. In the continuous motion, (i.e. motion-based) implementation, the sensors track a continuous motion of the footrest, such as a rotation or tilt, and function switch 304 transmits the continuous motion to processor 118A. For example, a double-tilt-and-release motion of the foot of surgeon 120 exerted on footrest 306 is sensed as a continuous motion and provided to processor 118A. In the discrete implementation, the sensors sense discrete states of footrest 306. Thus the continuous double-tilt-and-release motion above is sensed as a sequence of four discrete states: tilt-on, rest, tilt-on, rest. It is to be noted that a "sequence" in this embodiment may include only a single state. Additionally or alternatively, a sequence may be defined by the duration of a state, e.g. a long versus short press or tilt. In some embodiments, processor 118A determines a resting state when no other state is reported, or no motion is reported or received for a predetermined time period.

Figure 3B:
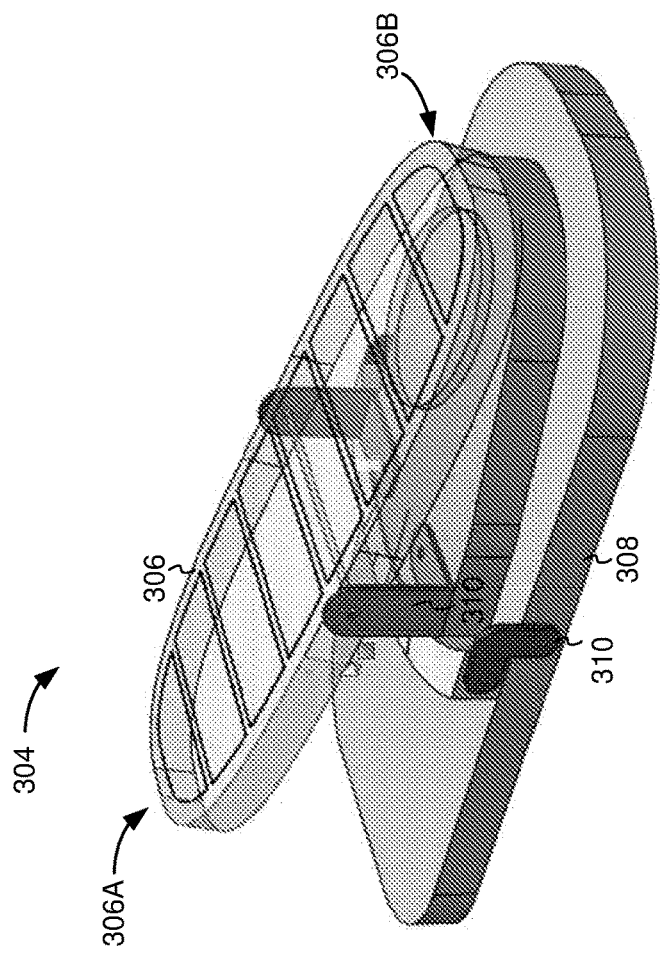
FIGS. 3A-3D, taken together with FIGS. 1A-1D, illustrate an exemplary function switch for controlling a surgical system, constructed and operative in accordance with another embodiment of the disclosed technique.
Figure 3A:
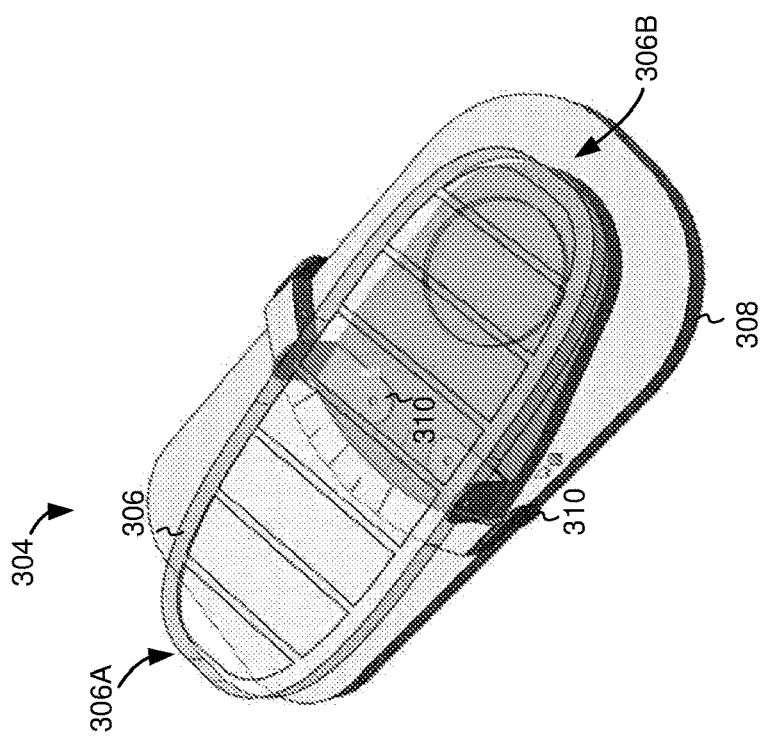
Figure 3D:
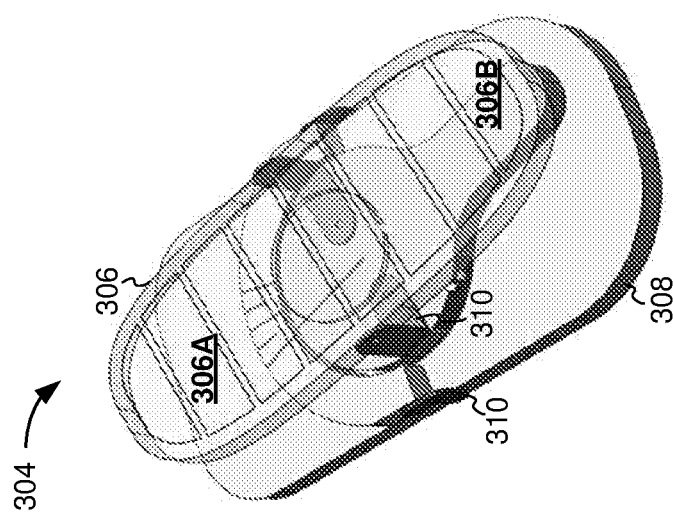
Figure 3C:
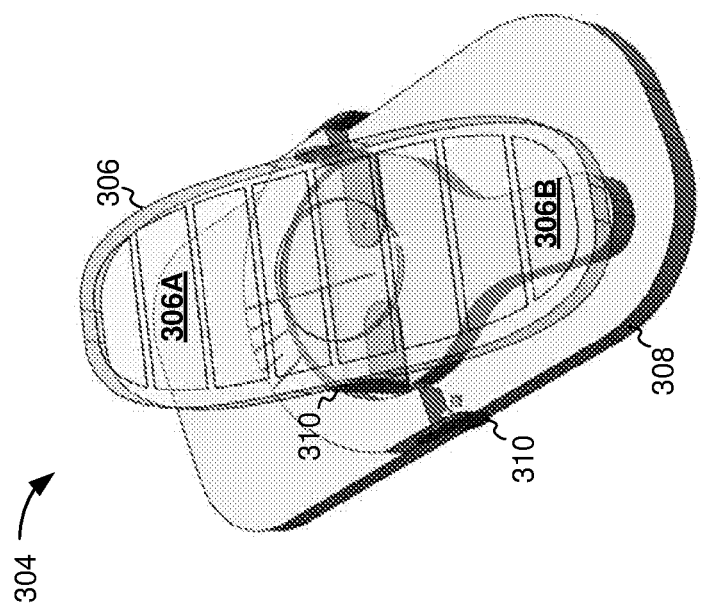

Surgeon 120 rests his foot on footrest 306. Pivots 310 allow surgeon 120 to manipulate the position and orientation of footrest 306 with respect to platform 308 to control system 100. The resting (default) state of function switch 304 allows surgeon 120 to comfortably rest his foot. Footrest 306 tilts in response to pressure exerted by the heel at the rear portion 306B of footrest, or forefoot of surgeon 120 at the front portion 306A of footrest. When no tilting force is exerted, the footrest will return to the default state, and when no rotation force is exerted, the footrest will return to the default un-rotated state. This may be implemented for example with one or more springs (not shown). The default state may be tilted so it is more comfortable to rest the foot for long periods of time, while still allowing for further tilting (pressing) with the heel. The axes may be arranged such that the rotation is around the heel (FIGS. 3A-3B), or alternatively around the center of the foot (FIGS. 3C-3D). Sensing the tilt and rotation may be implemented in any way known in the art, such as by using micro-switches and/or encoders (e.g. for sensing a discrete state), or alternatively for example with an IMU (e.g., for tracking a continuous motion).

In some embodiments, each user may configure the rotation and/or tilt of the function switch according to personal preferences (i.e. the amount of rotation and/or tilt required for switching between two adjacent functions in the slider and/or for switching between sliders may be user-configurable). In some embodiments, a bridge (not shown) is added to the embodiments of FIGS. 3A-3D, so the user can rest the foot on the bridge without causing any tilt. In some embodiments, the rotatable footrest may allow for additional tilting options. For example, the footrest may also allow sideway tilts in addition to the backward and forward tilts (not shown).

Figures 4A, 4B, 4C:
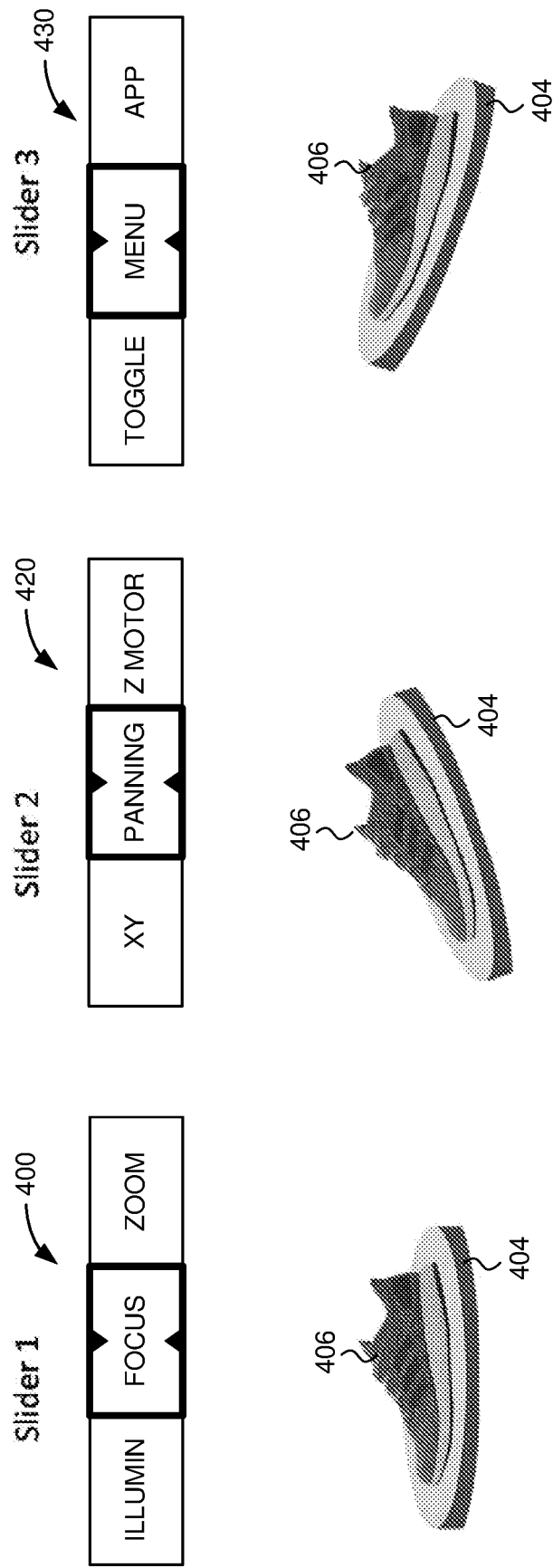
FIGS. 4A-4D, taken together with FIGS. 1A-1D, illustrate another exemplary user interface for enabling and controlling functions of a surgical system via three different function sliders, constructed and operative in accordance with a further embodiment of the disclosed technique.

Reference is now made to FIGS. 4A-4D, which taken together with FIGS. 1A-1D, illustrate another exemplary user interface for enabling and controlling functions of a surgical system via three different function sliders 400, 420, and 430, constructed and operative in accordance with a further embodiment of the disclosed technique. It is to be noted that any of sliders 400, 420, and 430 are entirely optional and the surgeon may interface with system 100 via the function switch with the sliders disabled (i.e., not displayed), such as when the surgeon has memorized the different motions for enabling the different functions. Each of FIGS. 4A-4C illustrates one of function sliders 400, 420, and 430 that may be invoked separately by manipulating a function switch 404, corresponding to function switch 104, with the foot 406. The tilt that surgeon 120 imposes on function switch 404 with the foot 406 determines which of function sliders 400, 420, and 430 is presented via HMD 103. Referring to FIG. 4A, surgeon 120 invokes default function slider 400 (slider 1) by moving the footrest of function switch 404 with foot 406, such as a tilt forward and back to the home position (i.e. pressing forward and releasing, without holding the footrest pressed). Processor 118A displays first function slider 400 to surgeon 120 via HMD 103 when surgeon 120 keeps function switch 404 (i.e. un-tilted) with respect to the default state. Function slider 400 presents the Illumin, Focus and Zoom functions to surgeon 120. Referring to FIG. 4B, processor 118A displays second function slider 420 when surgeon 120 presses foot 406 forwards with the forefoot, and function switch 404 is tilted forwards with respect to the floor. Function slider 420 presents to surgeon 120 the XY, Panning, and Z motor functions. Referring to FIG. 4C, processor 118A displays third function slider 430 via HMD 103 when surgeon 120 presses foot 406 presses backwards with the heel, and function switch 404 is tilted backwards with respect to the floor. Function slider 430 presents to surgeon 120 the Toggle, Menu, and App functions. The size of the tilt illustrated in FIGS. 4A-4C while pressing down is exaggerated for the sake of clarity. The default (resting) state is shown as horizontal, but the default state may be tilted so it is more comfortable to rest the foot for long periods of time.

The following list of functions is intended as an exemplary grouping of functions over multiple sliders, i.e. function sliders 400, 410, and 430 of FIGS. 4A-4C, respectively. It is to be noted that additional sliders, functions and implementations are possible. Surgeon 120 invokes the default slider, i.e. function slider 400, with a quick forward tilt of function switch 404 (without holding) to select focus (default option), or rotating left or right (with or without holding, depending on the implementation as further described below) to select zoom or illumination, respectively:

Focus (center)
Zoom (left)
Illumination (right)

After surgeon 120 invokes the slider using any of the above implementations, surgeon 120 may change the selected function by rotating the footrest of function switch 404. In some embodiments, once surgeon 120 initiates head motions tracked by head tracker 102, the selected function may not be changed until the process is terminated and surgeon 120 invokes the slider again.

Surgeon 120 may invoke second function slider 420 (FIG. 4B) by tilting forward function switch 404, and holding this position, illustrated herein below Alternatively, surgeon 120 may invoke second function slider 420 by tilting forward the footrest twice without holding (not shown). Second function slider 420 is invoked with the center function (Panning) selected as the default. Rotating footrest of function switch 414 left or right rotation (with or without holding, as described below) selects the left or right functions, respectively:

Panning (center)
XY motors (left)
Z motor (right)

Surgeon 120 may invoke third function slider 430 (FIG. 4C) by tilting function switch 404 backwards with foot 406, and holding this position, illustrated herein below. Alternatively, surgeon 120 invokes third function slider 430 by tilting the footrest of function switch 404 backward without holding (not shown). Surgeon 120 selects the left of right functions displayed on function slider 430 by rotating the heel of foot 406 on function switch 404 either left or right, respectively (with or without holding, as described below):

Menu (center)
Toggle (left)
App (right)

In some embodiments, surgeon 120 may invoke function sliders 400, 420, and 430 by pressing function switch 404 once to invoke first function slider 400, pressing function switch 404 twice to invoke second function slider 420, and pressing function switch 404 three times to invoke third function slider 430. Alternatively, to invoke first function slider 400, surgeon 120 may press and then release the footrest of function switch 404 after a first predetermined time period. To invoke second function slider 420, surgeon 120 may press and then release the footrest of function switch 404 after a second (longer) predetermined time period. To invoke third function slider 430, surgeon 120 may press and then release footrest of function switch 404 after a third predetermined time period. Once one of function sliders 400, 420, and 430 have been invoked, surgeon 120 may rotate the footrest of function switch 404 to navigate the options displayed on the invoked slider.

Once surgeon 120 has invoked one of function sliders 400, 420, and 430, has selected a single function, and has begun performing head motions tracked by head tracker 102, there are ways to implement the display of the invoked slider. In one implementation, processor 118A continues to display the invoked slider on HMD 103 and highlights the function currently controlled by surgeon 120, in a manner to distinguish before and after initiating the head motions. In another implementation, processor 118A hides the invoked slider from the display of HMD 103, and only displays the controlled function on HMD 103.

Figure 4D:
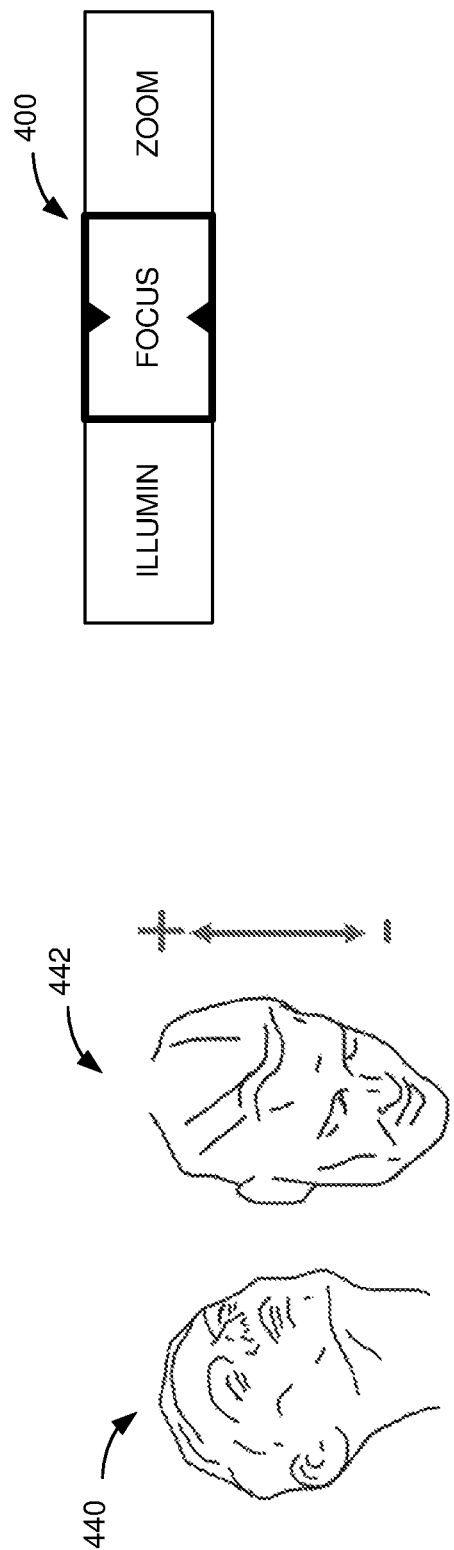

Referring to FIG. 4D, a method for interfacing with surgical system 100 via function slider 400 using corresponding head motions tracked with head tracker 102 is shown. Two head motions are shown for controlling function slider 400: 440 (head up) and 442 (head down). The head motions are exaggerated for the sake of clarity. Head tracker 102 may be integrated with HMD 103. In an alternative implementation, head tracker 102 may be implemented by a camera positioned in the operating theater. Processor 118A highlights the display of the selected function (e.g. "Focus") of function slider 400 on HMD 103 to indicate that it is enabled. Surgeon 120 controls the selected function by performing head motions 440 (head up) and 442 (head down). When surgeon 120 maintains the head in a static, or stationary position for a predetermined period of time (e.g. 1 second), processor 118A disables the "Focus" function and function slider 400 disappears. Alternatively, once surgeon 120 has begun performing the head motions, surgeon 120 may terminate the action by tilting the footrest of function switch 404 (without holding). In response, processor 118A hides slider from the display.

Figure 4G:
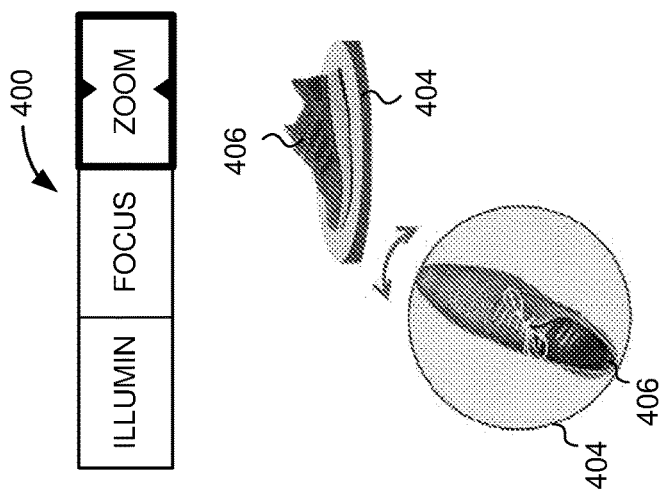
FIGS. 4E-4G, taken together with FIGS. 1A-1D and 4A-4D, illustrate an exemplary technique for interfacing with the slider of FIG. 4A, constructed and operative in accordance with another embodiment of the disclosed technique.
Figure 4F:
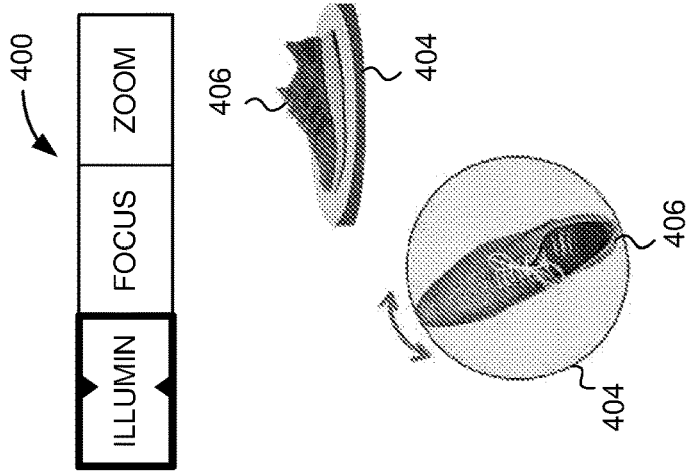
Figure 4E:
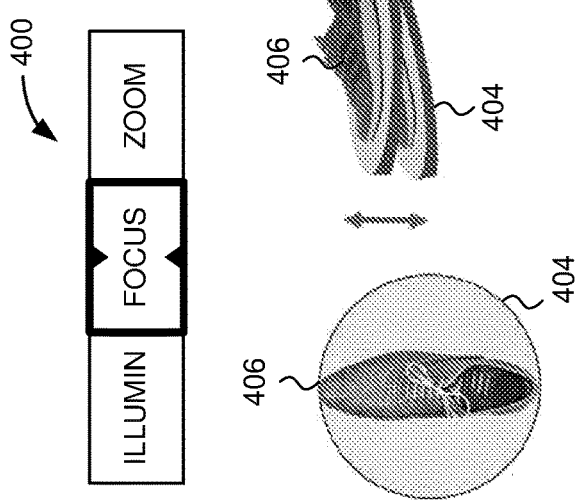

Reference is now made to FIGS. 4E-4G, which taken together with FIGS. 1A-1D and 4A-4D, illustrate an exemplary technique for interfacing with function slider 400 of FIG. 4A, constructed and operative in accordance with another embodiment of the disclosed technique. To enable the "Focus" function on function slider 400, Option #1: surgeon 120 presses foot 406 down and releases function switch 404, without rotating (FIG. 4E). Alternatively, surgeon 120 performs any small transient movement to invoke the default slider. The enablement may be automatically terminated after the head of surgeon 120 is stationary for a predefined time period. Option #2: surgeon 120 presses foot 406 down and releases function switch 404 without rotating foot 406 for locking the enablement of the "Focus" function. Surgeon 120 presses foot 406 down and releases to terminate the enablement of the "Focus" function. Termination according to option #3, may be achieved by any of the above actions (e.g. whichever comes first).

Referring to FIG. 4F, to enable the "Illumination" function according to option #1, surgeon 120 rotates foot 406 left on function switch 404 and releases, without tilting. Processor 118A terminates the enablement of the "Illumination" function with a timer. Alternatively, surgeon 120 may terminate the enable by pressing foot 406 down and releasing function switch 404. To enable the "illumination" function according to option #2, surgeon 120 rotates foot 406 left on function switch 404, without tilting function switch 404. To terminate the enablement of the "illumination", surgeon 120 rotates foot 406 back to center on function switch 404.

Referring to FIG. 4G, to enable the "Zoom" function, option #1, surgeon rotates foot 406 right and releases function switch 404, without tilting function switch 404. Processor 118A may terminate the enablement of the "Zoom" function with a timer. Alternatively, surgeon may terminate the enablement of the "Zoom" function by pressing foot 406 down and releasing function switch 404. To enable the "Zoom" function according to option #2, surgeon 120 rotates foot 406 right on function switch 404, without tilting function switch 404. Surgeon 120 rotates foot 406 back to center on function switch 404 to terminate enablement of "Zoom".

Figures 4H, 4I, 4J:
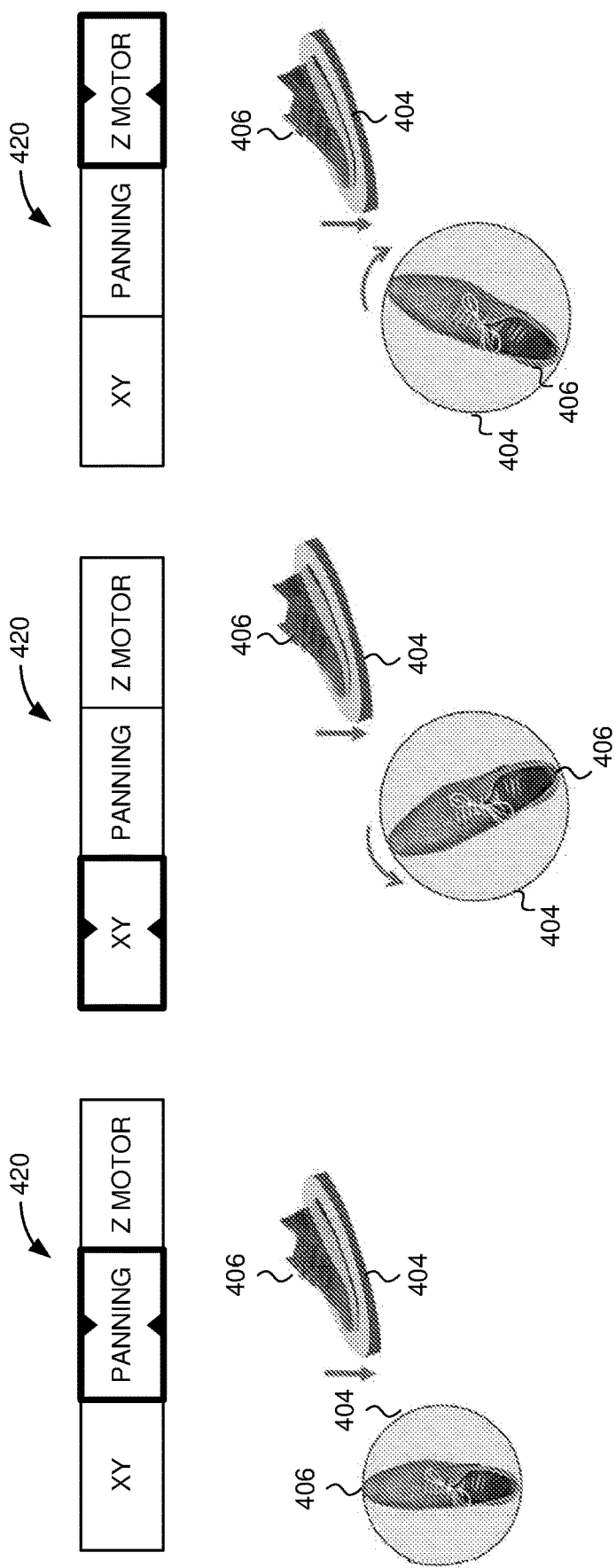
FIGS. 4H-4J, taken together with FIGS. 1A-1D and 4A-4D, illustrate an exemplary technique for interfacing with the slider of FIG. 4B, constructed and operative in accordance with a further embodiment of the disclosed technique.

Reference is now made to FIGS. 4H-4J, which taken together with FIGS. 1A-1D and 4A-4D, illustrate an exemplary technique for interfacing with function slider 420 of FIG. 4B, constructed and operative in accordance with a further embodiment of the disclosed technique. To enable the "Panning" function (FIG. 4H), surgeon 120 presses forward function switch 404, without rotating. To enable the XY motors (FIG. 4I), surgeon 120 presses forward function switch 404 with foot 406 and rotates left. To enable the "Z motor" function (FIG. 4J), surgeon 120 presses forward function switch 404 with foot 406 and rotates right. In these three cases surgeon 120 terminates the enablement of the function by releasing the footrest of function switch 404 (i.e., returning function switch 404 to the neutral position, un-rotated and un-tilted). Alternatively (not shown), surgeon 120 may invoke second function slider 420 by double-tilting footrest of function switch 404 forward (without holding), keep the footrest un-rotated for selecting "Panning", or rotate the footrest for selecting "XY" or "Z" and releasing. In these examples, surgeon 120 may terminate the enablement of the functions by a forward tilt and release. Alternatively, surgeon 120 may invoke second function slider 420 with a long forward tilt and release of function switch 404 (i.e. as opposed to a short forward tilt and release for invoking first function slider 400).

Figure 4K:
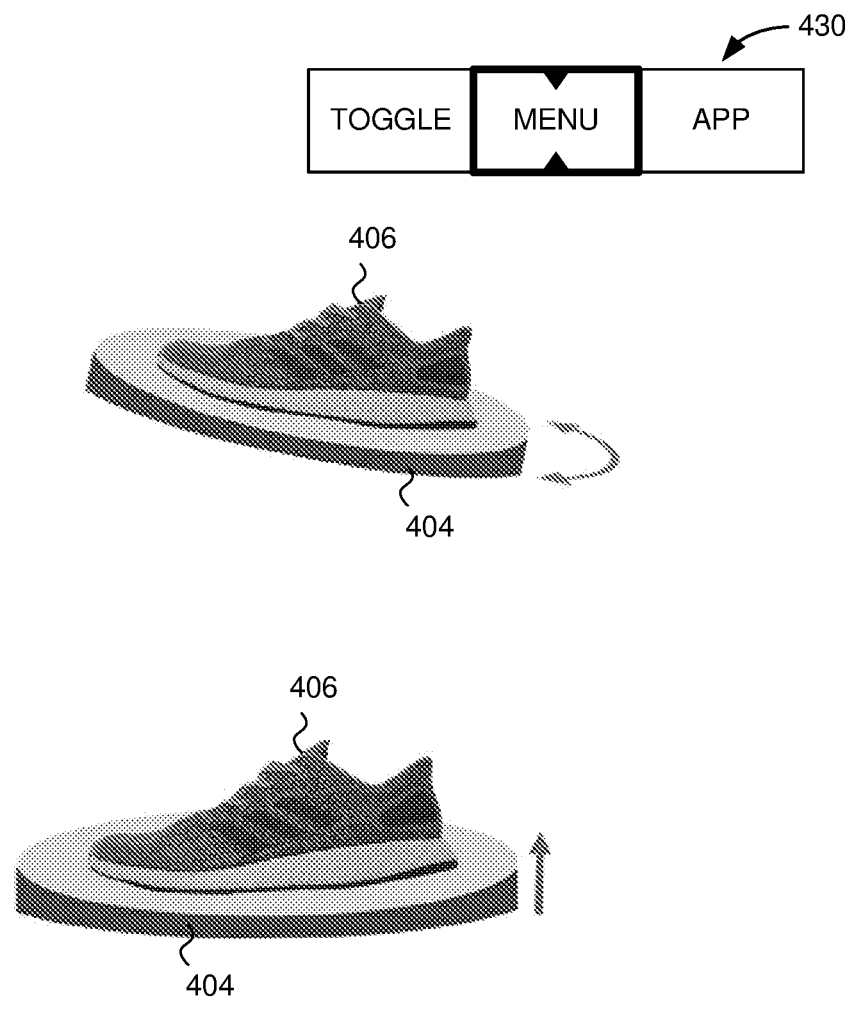
FIG. 4K taken together with FIGS. 1A-1D and 4A-4D, illustrate an exemplary technique for interfacing with the slider of FIG. 4C, constructed and operative in accordance with another embodiment of the disclosed technique.

Referring to FIG. 4K, which taken together with FIGS. 1A-1D and 4A-4D, illustrate an exemplary technique for interfacing with function slider 430 of FIG. 4C, constructed and operative in accordance with another embodiment of the disclosed technique. When surgeon 120 presses the heel of foot 406 on function switch 404, processor 118A displays function slider 430 (slider 3) on HMD 103 with the "Menu" option selected. Surgeon 120 can switch between the functions by rotating foot 406 on function switch 404. The "Toggle" mode allows surgeon 120 to toggle between the current mode and the previously used mode (e.g. "anterior", "flat, wide lens", "other"). After the "Toggle" function is highlighted, surgeon 120 releases function switch 404 to toggle.

The "Menu" mode invokes the main menu. Surgeon 120 navigates the menu with head motions tracked by head tracker 102, and releases function switch 404 with foot 406 to activate a menu item. The "App" function allows surgeon 120 to operate a working app. Surgeon 120 keeps function switch 404 pressed using the heel of foot 406 to enable head motions for operating the app (or for a quick access of an app when applicable, as described above). Surgeon 120 releases function switch 404 with foot 406 to stop the enable. Alternatively (not shown), surgeon 120 may invoke third function slider 430 by tilting the footrest of function switch 404 backwards without holding (i.e. returning to the un-tilted state), keep the footrest un-rotated for selecting "Menu", or rotate the footrest for selecting "Toggle" or "App" and releasing. In these examples a forward tilt and release of function switch 404 may be used for activating a menu item or for terminating an enable. Similarly, the quick access function (i.e. the toggle or the app when applicable) is activated when the rotation is released on function switch 404.

In another embodiment (not shown), when multiple sliders are being used, processor 118A may continue switching the display of the various sliders as long as surgeon 120 presses (tilts) the footrest of function switch 404. For example, processor 118A displays first function slider 400, and after a predetermined time period processor 118A replaces function slider 400 and displays second function slider 420 instead. After an additional predetermined time period, processor 118A replaces the display of second function slider 420 by displaying third function slider 430, in place of second function slider 420, and so on, in a cyclical manner The predetermined time periods between switching between the sliders may be configurable. Surgeon 120 selects the slider that is currently displayed by releasing the footrest of function switch 404. Surgeon 120 may navigate among the functions displayed in the selected slider by rotating the footrest of function switch 404 with foot 406. In this embodiment the footrest tilts forwards only, and the default (resting) position of the footrest is slightly tilted with the heel comfortably lower.

Figure 5A:
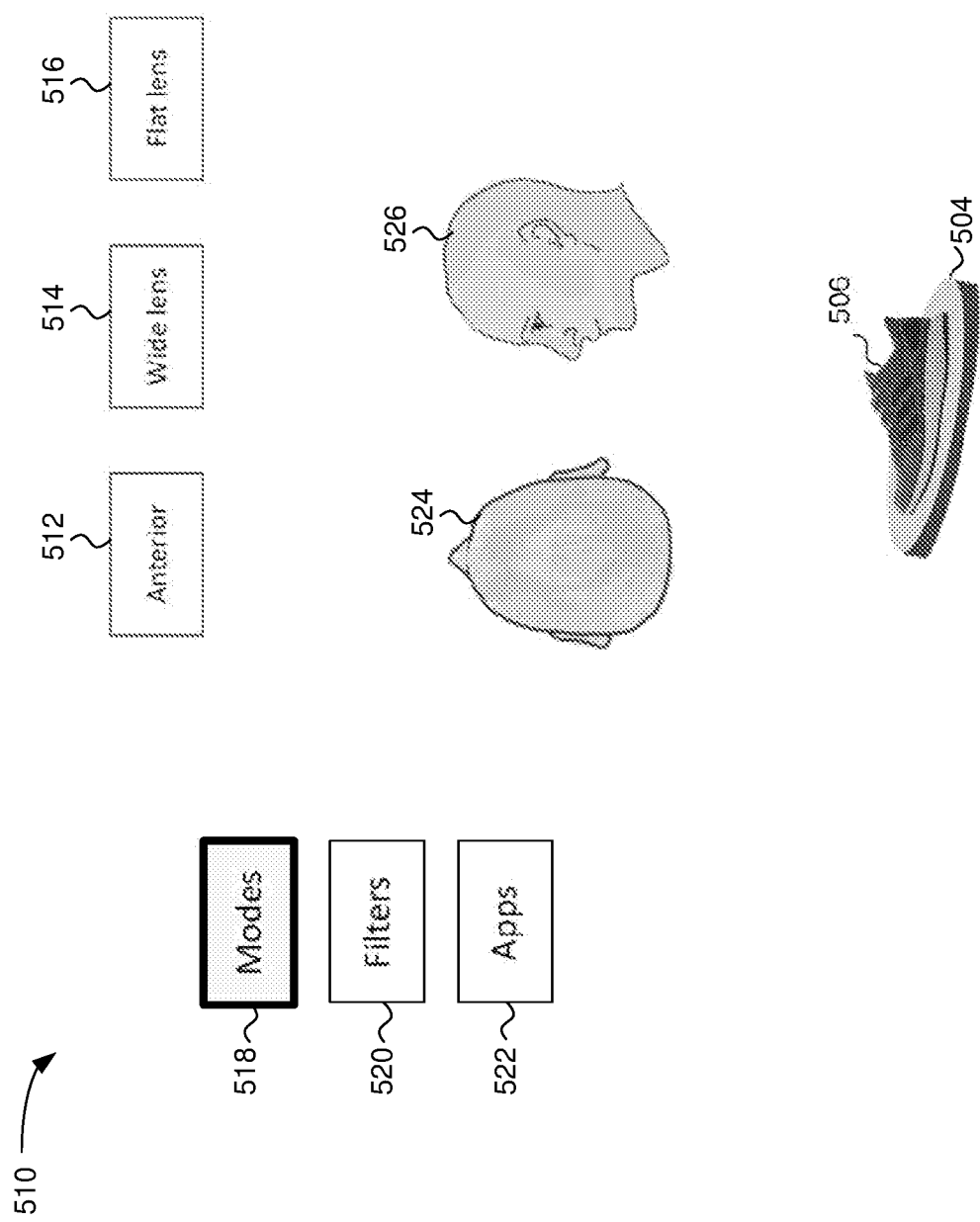
FIGS. 5A-5I, taken together with FIGS. 1A-1D, illustrate a technique for navigating a menu using a function switch in conjunction with one or more head motions, constructed and operative in accordance with a further embodiment of the disclosed technique.
Figure 5B:
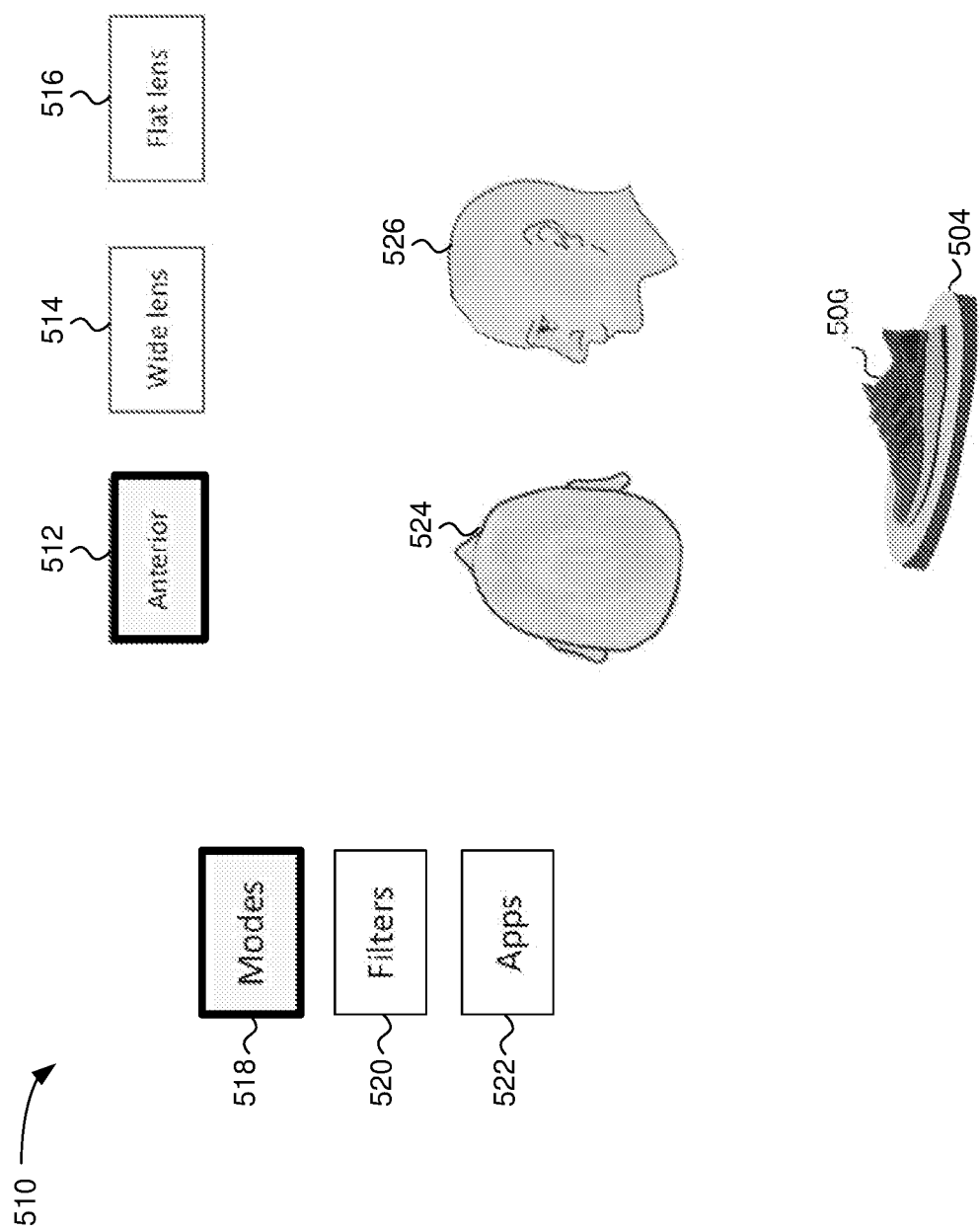
Figure 5C:
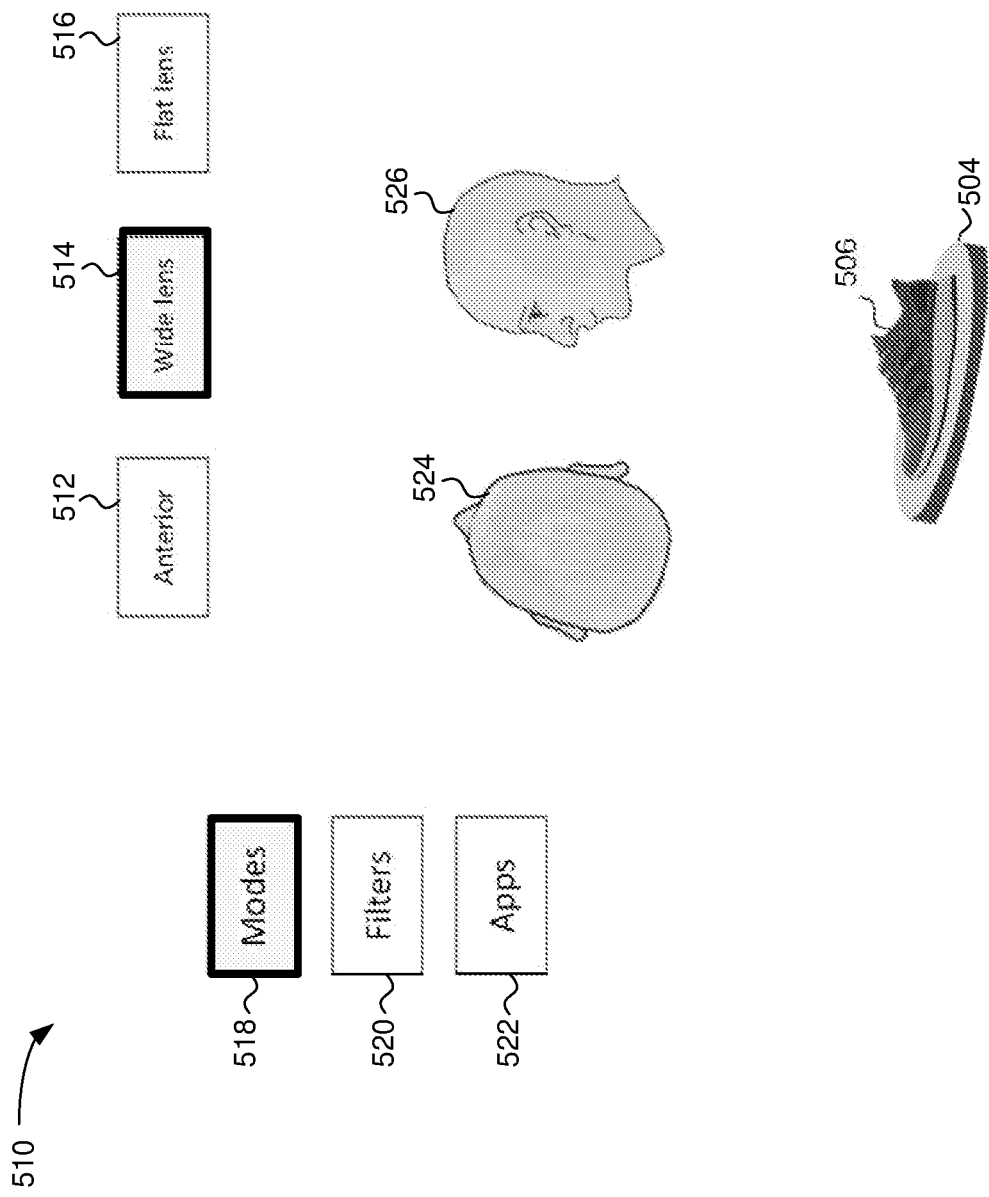
Figure 5D:
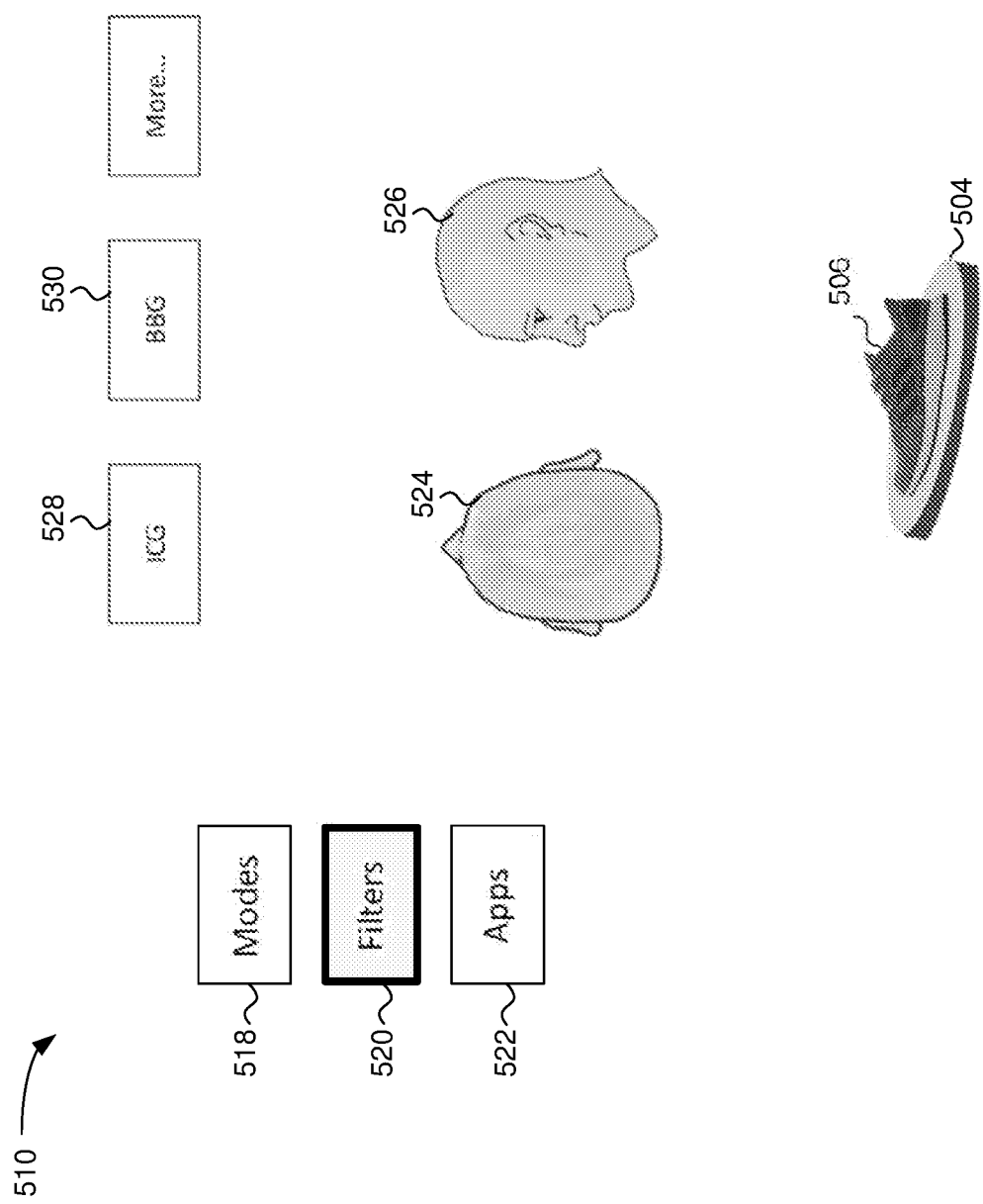
Figure 5E:
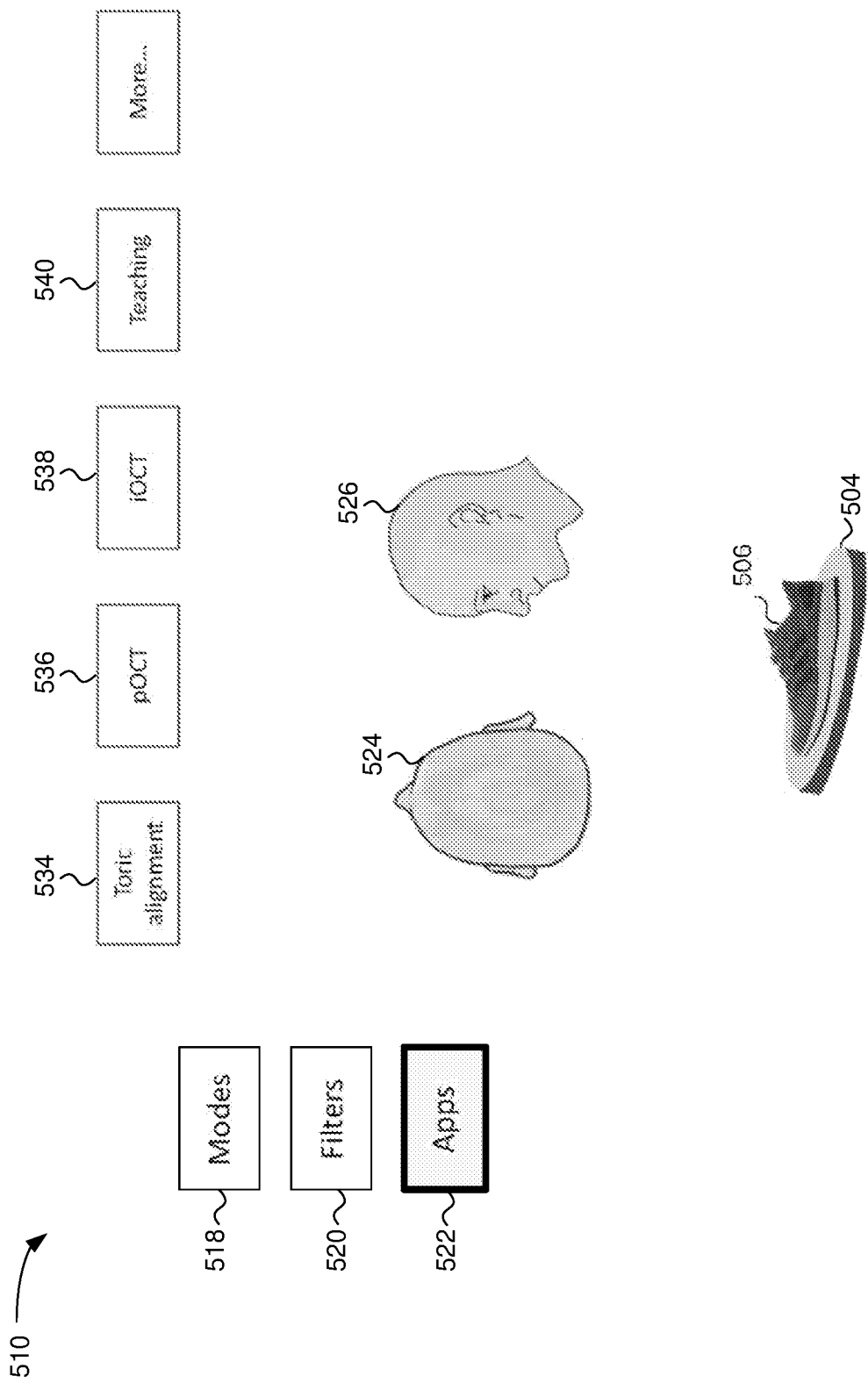

Reference is now made to FIGS. 5A-5I which taken together with FIGS. 1A-1D, illustrate a technique for navigating a menu using a function switch in conjunction with one or more head motions, constructed and operative in accordance with a further embodiment of the disclosed technique. Menu 510 includes three menu items: "Modes" 518, "Filters" 520, and "Apps" 522 displayed on the left, and arranged vertically (top to bottom). FIG. 5A shows the "Modes" menu item 518 highlighted, with the three sub-menu items of "Modes" 518: "Anterior" 512, "Wide Lens" 514, and "Flat lens" 516, displayed at the top, arranged horizontally (left to right). FIG. 5D shows the "Filters" menu item 520 highlighted, with the two sub-menu items of "Filters" 520: "ICG" 528, and "BBG" 530 displayed at the top, arranged horizontally. Filters 520 may include additional sub-menu items (e.g. "More . . . "). FIG. 5E shows the "Apps" menu item 522 highlighted, with the four sub-menu items of "Apps" 522: "Toric Alignment" 534, "pOCT" 536, "iOCT" 538, and "Teaching" 540, displayed at the top, arranged horizontally. Apps 522 may include additional sub-menu items (e.g. "More . . . ").

Surgeon 120 invokes menu 510 via function switch 504, representative of function switch 104, with his foot 506. Processor 118A receives the foot motions sensed by function switch 104 and displays menu 510 to surgeon 120 in response. The display in the description that follows may be HMD 103, or alternatively, may be a stand-alone display, such as screen 108. Once menu 510 has been invoked, surgeon 120 navigates menu 510 by moving his head, shown from a top view 524 to illustrate right-left turns of the head, and a profile view 526 to illustrate up-down tilts of the head.

Referring to FIG. 5A, after selecting to invoke menu 510 via function switch 504, as described above with respect to FIG. 4K, surgeon 120 navigates the displayed menu 510 with one or more head motions tracked by head tracker 102. Processor 118A receives the tracked head motions from head tracker 102 and modifies the display of menu 510 accordingly, such as by highlighting certain menu items to indicate their selection and activation.

To navigate between the menu items: "Modes" 518, "Filters" 520, and "Apps" 522, arranged vertically on the left side of the display, surgeon 120 tilts the head up and down, accordingly. The head motions are sensed by head tracker 102 and provided to processor 118A, which modifies the display to reflect the menu item selected by the head motions of surgeon 120. The menu items displayed to surgeon 120 may vary, depending on the current system mode, procedure type, app activation, user preferences, etc. To navigate the sub-menu items, arranged horizontally on top, surgeon 120 turns his head left and right. FIG. 5A shows surgeon 120 with his head oriented in a neutral position, with "Modes" 518 selected (highlighted).

Turning to FIG. 5B, surgeon 120 maintains a neutral position 526 (no tilt) to stay in "Modes" 518 on main menu 510. While maintaining the head in the neutral position (526), surgeon 120 turns the head to the right (524) to select the "Anterior" function 512 on the sub-menu, shown highlighted. The rightward tilt head motion is tracked by head tracker 102 and transmitted to processor 118A, which modifies the display accordingly by highlighting "Anterior" 512 to indicate that it has been selected.

Turning to FIG. 5C, surgeon 120 maintains the neutral, no tilt position (526) to stay in "Modes" 518 on main menu 510. While maintaining the head in the neutral, no tilt position (526), surgeon 120 turns his head further to the right (524) to select the 'Wide Lens" function 514 positioned to the right of "Anterior" 512 in the sub-menu. Head tracker 102 senses the further rightward head turn 524 and provides the sensed motion to processor 118A. Processor 118A modifies the display by highlighting the "Wide Lens" 514 to indicate that it has been selected.

Turning to FIG. 5D, surgeon 120 faces straight forwards 524 (no turn), however he tilts the head downwards (526) to select the second option, "Filters" 520, from main menu 510. Processor 118A receives the tracked head motion from head tracker 102 and displays the sub-menu corresponding to the "Filters" 520 menu, arranged horizontally on top. The sub-menu options are: "ICG" 528 and "BBG" 530.

Turning to FIG. 5E, surgeon 120 faces straight forwards 524 (no turn), and tilts the head further downwards (526) to select the third option, "Apps" 522, from main menu 510. Processor 118A receives the tracked downwards tilt head motion from head tracker 102, highlights the display of "Apps" 522 to indicate its selection via head motion. Processor 118A displays the sub-menu corresponding to "Apps" 522 on top, arranged horizontally. The sub-menu options are: "Toric" alignment 534 "pOCT" 536, "iOCT" 538, and "Teaching" 540.

Figure 5F:
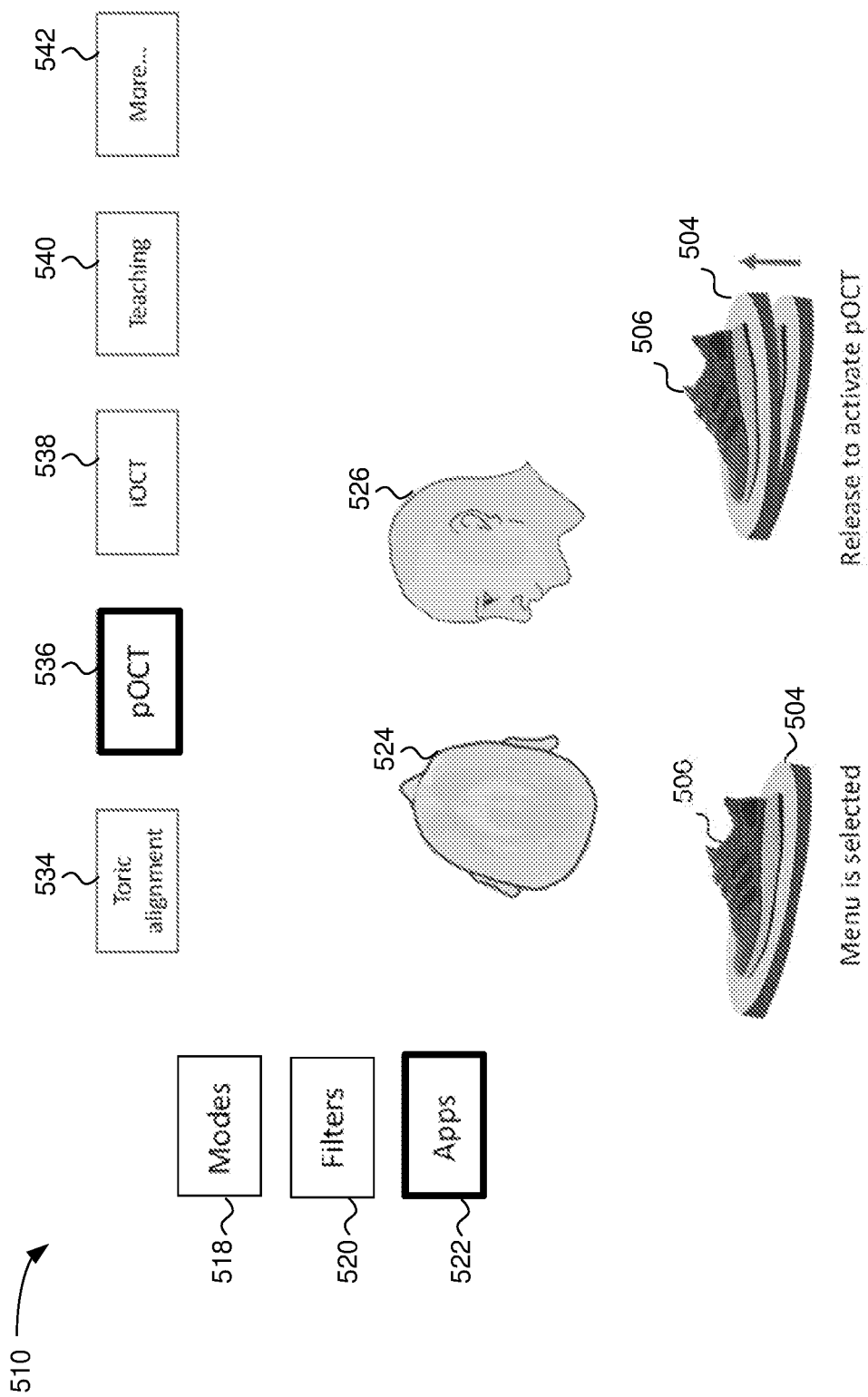

Turning to FIG. 5F, surgeon 120 maintains the downwards tilt of the head 526 to select "Apps" 522 from main menu 510 and turns the head in a rightward rotation 524 to select "pOCT" 536 from the sub-menu, positioned to the right of "Toric alignment" 534. Processor 118A receives the tracked rightwards turn from head tracker 102 and highlights the display of "pOCT" 536 to indicates its selection via head motion. To activate the pOCT mode, surgeon 120 releases function switch 504 by lifting the heel of foot 506 off of function switch 504. Processor 118A receives the lower body motion sensed by function switch and activates the pOCT mode. In some embodiments, processor 118A only highlights the display of "pOCT" 536 after activation by both head motion and foot motion.

Figure 5G:
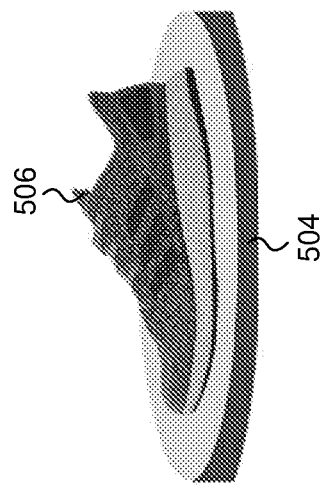
Figure 5G:
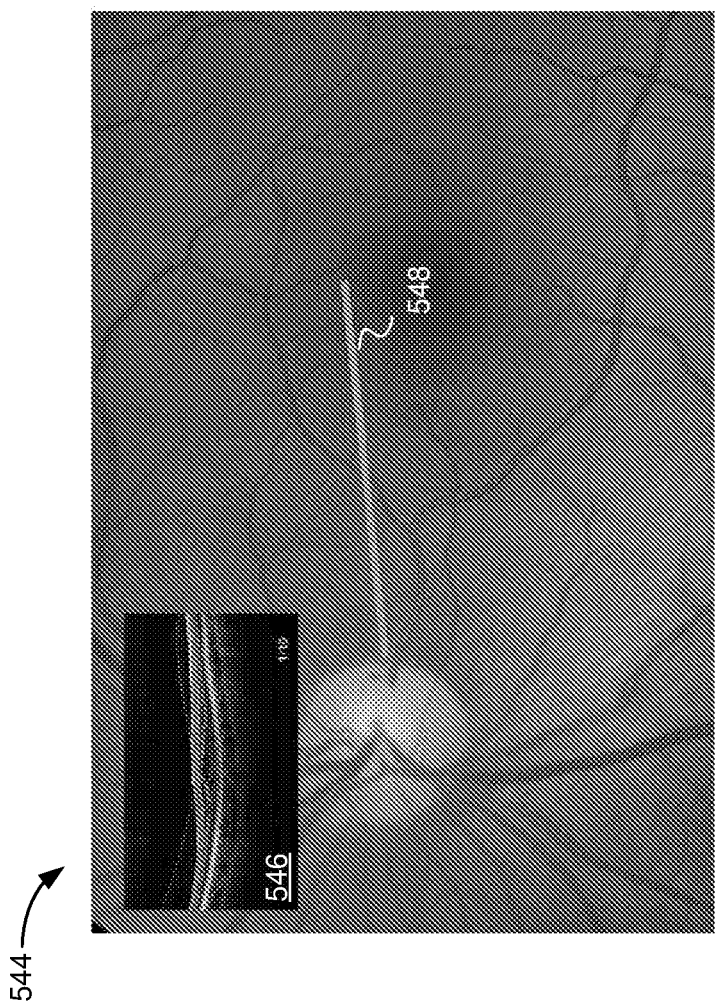

Turning to FIG. 5G, the display via HMD 103 is illustrated after surgeon 120 has activated the "pOCT" 536 via menu 510 by releasing function switch 504 with foot 506, as described above. Processor 118A displays a live image 544 with a B-scan image 546, obtained using optical coherence tomography (OCT), overlaid at the upper left corner in a "picture in picture" (PIP). Processor 118A displays a line 548 to indicate the area on live image 544 that corresponds to B-scan image 546.

Figure 5H:
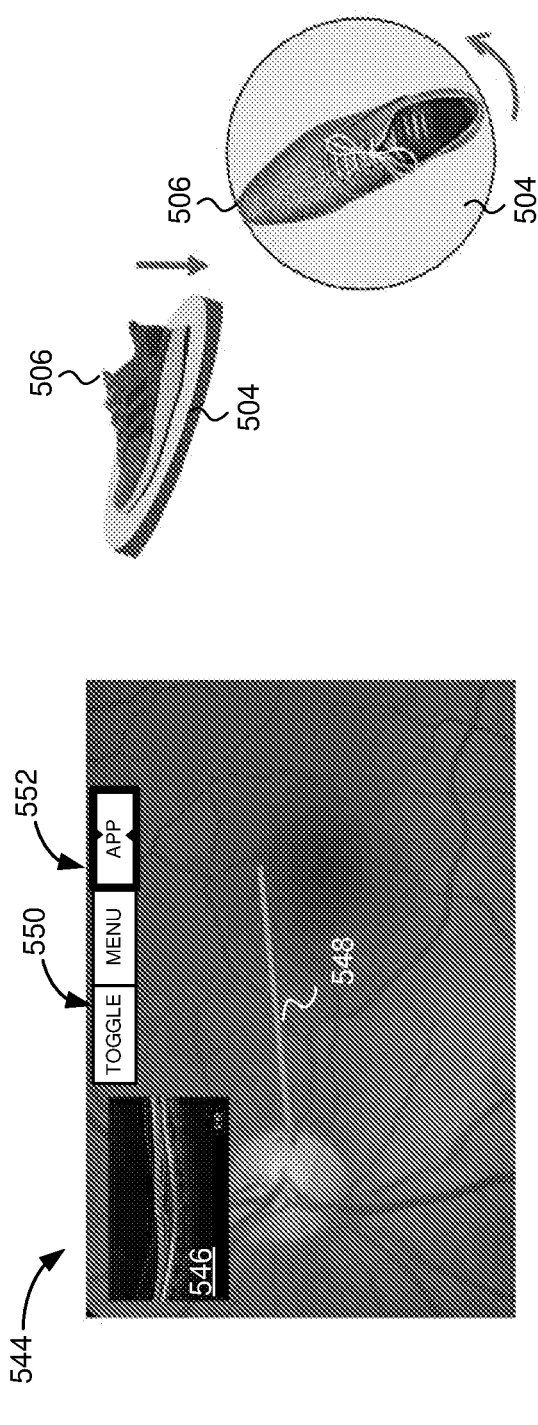
Figure 5H:
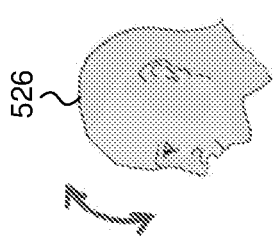

Turning to FIG. 5H, surgeon 120 enables the "App" function 552 of function slider 550 by pressing on function switch 504 with the heel of foot 506 while rotating function switch 504 to the right with the heel to of foot 506 (foot motions shown on right hand side). Processor 118A displays function slider 550 at the top center of live image 544 and keeps "App" 552 (far-most right option) of function slider 550 enabled while foot 506 is pressed down and rotates function switch 504 rightwards. While "App" is enabled by pressing down and turning function switch 504 with foot 506, surgeon 120 scrolls through a library of B-scan images 546 using head motions (e.g. up-down motions) to adjust the position of line 548 on live image 544. Head tracker 102 tracks the head motions and provides the head motion to processor 118A. Processor 118A adjusts the position of line 548 to correspond to the relative up-down tilt angle of head 526, e.g. if head 526 tilts upwards, processor 118A shifts line 548 upwards on live image 544 by a proportional distance. Similarly, if head 526 tilts downwards, processor 118A shifts line 548 downwards on live image 544 by a proportional distance. Processor 118A updates B-scan image 546, displayed in PIP overlaid on live image 544, to correspond to the current position of line 548 on live image 544.

Figure 5I:
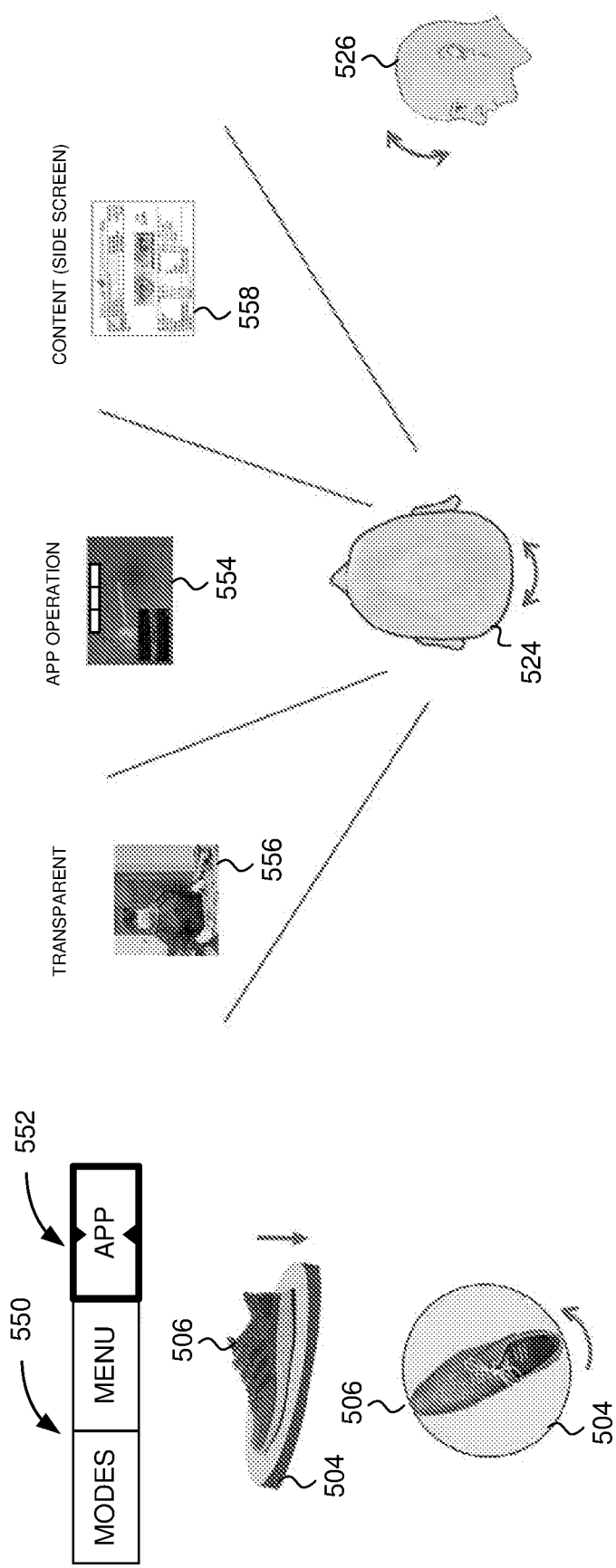

Turning to FIG. 5I, a technique for maneuvering between the side-screen and transparent system modes is shown. Surgeon 120 enables "App" 552 of function slider 550 by pressing down and rotating function switch 504 to the right with the heel of foot 506. Function switch 504 provides the sensed motion to processor 118A. Surgeon 120 switches system modes by turning the head 524 beyond a predefined angle either to the right or to the left. Head tracker 102 tracks the head motion and provides the tracked head motion to processor 118A. As long as the head is aligned with the center region, processor 118A maintains the system mode unchanged. In the example of FIG. 5I, the system mode in the center region is "Posterior wide lens" 554 with the pOCT App activated, as described with regards to FIG. 5H.

When surgeon 120 tilts the head up-down (526) while "App" 552 is selected in this system mode, surgeon 120 may scroll within the preoperative OCT B-scans, as described with respect to FIG. 5H. When surgeon 120 turns the head from center to left, processor 118A receives the sensed motion from head tracker 102 and switches the system mode to the transparent mode 556, positioned to the left of "Posterior wide lens" 554. Processor 118A opens the shutter of HMD 103 and shuts down the electronic display of HMD 103, allowing surgeon 120 to view the operating theatre directly. When surgeon 120 turns his head from center to right, processor 118A receives the sensed motion from head tracker 102 and switches the system mode to the Content mode 558, positioned to the right of "Posterior wide lens" 554. In this mode, processor 118A displays a "side screen" comprising documents, notes and images preselected by surgeon 120. When surgeon 120 tilts the head up and down in this system mode, processor 118A allows surgeon 120 to scroll within the content displayed in the side screen. When surgeon 120 releases function switch 504 with foot 506, processor 118A reverts the system mode back to the original system mode. In this case the system mode associated with the center region is "Posterior wide lens", regardless of the orientation of the head of surgeon 120.

Alternatively, in some embodiments surgeon 120 is not required to hold the footrest of function switch 504 pressed backwards and rotated to keep "App" enabled. Rather, surgeon 120 enables the "App" function by a quick press and rotate of the footrest of function switch 504, followed by a release (i.e. return to the resting position). In this case, terminating the "App" function is done for example by a press (tilt) forward and release of the footrest of function switch 504.

In the above exemplary implementation, function switch 504 is implemented as a foot-enabled device placed on the floor and having a moveable footrest, however this is not intended to limit the invention, and additional implementations are possible. The various types of implementations may be categorized as localized implementations vs. wearable implementations.

In one embodiment, a wearable solution for the function switch may be based on a foot-wearable or leg-wearable wireless IMU for tracking and identifying predefined motion patterns of the user's foot or leg, such as tapping, dragging, rotating and swiping motions. This type of implementation may be better for surgical procedures where the surgeon tends to move during surgery. However, this type of solution may also require a method for disabling the function switch when the surgeon steps away from the surgical field, in order to avoid unintentional activation or enablement of a function. Alternatively, the surgeon may remove the wearable device when stepping away. A localized solution, i.e. a solution that is not wearable but physically located near the surgical field, may be suitable for procedures in which the surgeon tends to stand still or sit next to the surgical field. For instance in eye surgery the surgeon is usually sitting, and the duration of each operation is relatively short (especially in some types of procedures, like cataract surgery), many procedures are performed in succession, and the surgeon may walk away from the surgical field after each procedure. In this situation, it may be preferable if the function switch is not wearable, and implemented using one or more of a camera, touch sensor, electromagnetic sensor, acoustic sensor, and the like However in some neurosurgical procedures (head or spine) the surgeon may move around the patient, and the procedures may be relatively long. Therefore a wearable device might be a better solution for these cases.

In some embodiments, the function switch is implemented using a ball held by a socket integrated with the footrest. The socket includes one or more sensors to detect rotation of the ball. For example, the sensors may detect rotation about a forward axis and a side axis. The ball may protrude somewhat from the footrest to allow for easy and comfortable manipulation. The ball may be positioned towards the front of the footrest, and manipulated by the forefoot of the surgeon. Alternatively, the ball may be positioned in the middle and manipulated by the entire foot, or the ball may be positioned towards the rear of the footrest and manipulated by the heel of the surgeon.

In some embodiments, the function switch is implemented using a single joystick that is moveable in multiple directions (left-right, forwards-backwards, diagonally) as well as down (e.g. pressed).

In some embodiments, the function switch is implemented as a touchpad. The user may invoke various function sliders for instance by tapping on the touchpad (e.g. one tap for the default slider, two taps for a secondary slider, and so on). Alternatively, applying different pressures (i.e. hard, medium, soft) may invoke different sliders, each slider corresponding to a different tap pressure. The user may scroll within the functions in a slider for instance by dragging his foot over the touchpad, by rotating his foot, e.g. around the heel, or by swiping the foot (i.e. each swiping motion switches between two adjacent functions in the slider, depending on the direction of swiping). As in the example of the rotatable footrest, in some embodiments the user is required to maintain his foot position in order to keep the function enabled. In this case, moving the foot after the head motions are initiated terminates the enablement. In other embodiments, once the head motions are initiated the user is free to move the foot back to a comfortable resting position. In this case the enablement termination may be implemented using a timer, or for example by tapping the foot. In addition to invoking sliders and scrolling within a slider to select a function, one or more virtual buttons may be provided that are activated by tapping. To distinguish between tapping to invoke a slider and tapping for virtual buttons, the former may be performed without completely raising the foot from the touchpad (e.g. tapping with the heel or tapping with the forefoot), and the latter may be performed by raising the foot and tapping the touchpad at predefined locations, such as the corners. The system may be configured to identify the various types of tapping to allow for this implementation of virtual buttons. Virtual buttons may be used for quick access actions, such as toggling between system modes, saving a snapshot of the live video, and so on.

In some embodiments, the function switch is implemented by use of a tracker. The tracker may be easily configured to support various user preferences, such as where the tracker is mounted (i.e. wearable on the foot or thigh, chair-mounted, or alternatively a stationary tracker such as a camera tracking the foot), what motions are used to invoke sliders and to scroll between the various system functions, and how the selection and enablement process is initiated and ended. Trackers may be implemented by various technologies, such as a wireless MEMS-based IMU that enables to identify relative rotation and translation, tapping, swiping, and other gestures. It may be implemented as a small wearable solution, for instance on the foot or on the thigh, but also as a chair-mounted solution, for instance when the chair is rotatable. The wearable IMU solution may require a mechanism for disabling the tracking when stepping away from the surgical site, so as to not generate unintentional commands Such a mechanism may be based, for example, on proximity sensing such as RFID-based (e.g. based on an additional component attached to, or near the surgical table or the surgeon's chair). Alternatively such a mechanism may be based on sensing when the surgeon is not donning the HMD, or if the surgeon is donning the HMD but in a stow position. In these cases, the IMU signal may be ignored. Other tracking technologies may also be used, such as electro-magnetic (EM) tracking that requires a wearable component, optical tracking (e.g. a camera capturing foot movements), and other.

In some embodiments, a foot-based tracker is provided. The foot-based tracker may be a wearable tracking technology such as inertial or EM tracking, based on a wireless wearable tracker component, or other tracking technology, e.g. tracking the foot by a camera.

In some embodiments, a thigh-mounted tracker is provided. This may be implemented with IMU since the knee area is most likely not visible for an optical-based tracker due to the sterile covers, and the proximity to the possibly metallic surgical table inhibits the use of an EM tracker. The foot can remain rested (with minimal movement) on the floor, and selection is implemented by moving the knee (effectively by rotating the hip).

In some embodiments, a chair-mounted tracker is provided. The tracker may be implemented as a chair-mounted solution, for instance when the chair is rotatable. This may be suitable for a surgeon that operates while sitting, with forearms rested on the surgical table so the hands do not move when the chair is slightly swiveled. It doesn't suit a surgeon that uses the chair for arm-support or a surgeon that operates standing. The tapping that initiates the function slider can be implemented by tapping the chair's leg.

When using the tracking implementation, surgeon 120 may invoke any of the sliders described herein above by performing a predefined motion, such as by tapping the foot on function switch 104: e.g. a single tap, double tap, etc., or by tilting the foot (i.e. raising the heel or the forefoot), Alternatively, the function slider may be invoked through a combination of tapping and tilting, for instance a quick tilt forward or tap to invoke the slider with the central function selected (e.g. the focus); a left or right rotation to invoke the slider with the first off-center function (left or right) selected and keeping the foot rotated; and a left or right quick rotation without holding the foot rotated.

Surgeon 120 may scroll within the list of functions of the function sliders by performing the following motions. It is to be noted that this list is intended to be exemplary only. The surgeon may perform a rotation motion, i.e. by rotating his foot; rotating the foot about the forefoot, rotating the leg from the hip without moving the foot (i.e. by moving the knee, e.g. when a knee-wearable tracker is used), rotating a rotatable chair (e.g. by tracking the chair and not the leg or the foot). Alternatively, the surgeon may perform a vertical motion, i.e. an up-down motion using the heel or the forefoot. Alternatively, the surgeon may perform a swiping motion with the foot. Alternatively the surgeon may perform a horizontal movement, i.e. by dragging the foot sideways or forward and backwards. Surgeon 120 may receive an additional feedback such as an auditory or mechanical feedback while scrolling. For example: the user may feel a vibration when the selected function changes while scrolling generated by a vibration motor.

Once a function has been enabled, to control the function via head motions, in one embodiment the tracked foot (or leg or chair) may be required to stay still. In another embodiment the foot (or leg or chair) may move freely once the head motions commence. In principle, all the various embodiments that were described in relation to the rotatable footrest and the touchpad may also be implemented in a similar fashion with the tracking implementation.

In some embodiments, system 100 includes a speaker that announces the current slider, and/or the function that is currently selected, in order to allow the surgeon to continue focusing on an area of interest without having to divert his gaze to peripheral areas of the display. The slider and selected function may be indicated via both the HMD display and the speaker, or only via the HMD display, or only via the speaker.

Figure 6:
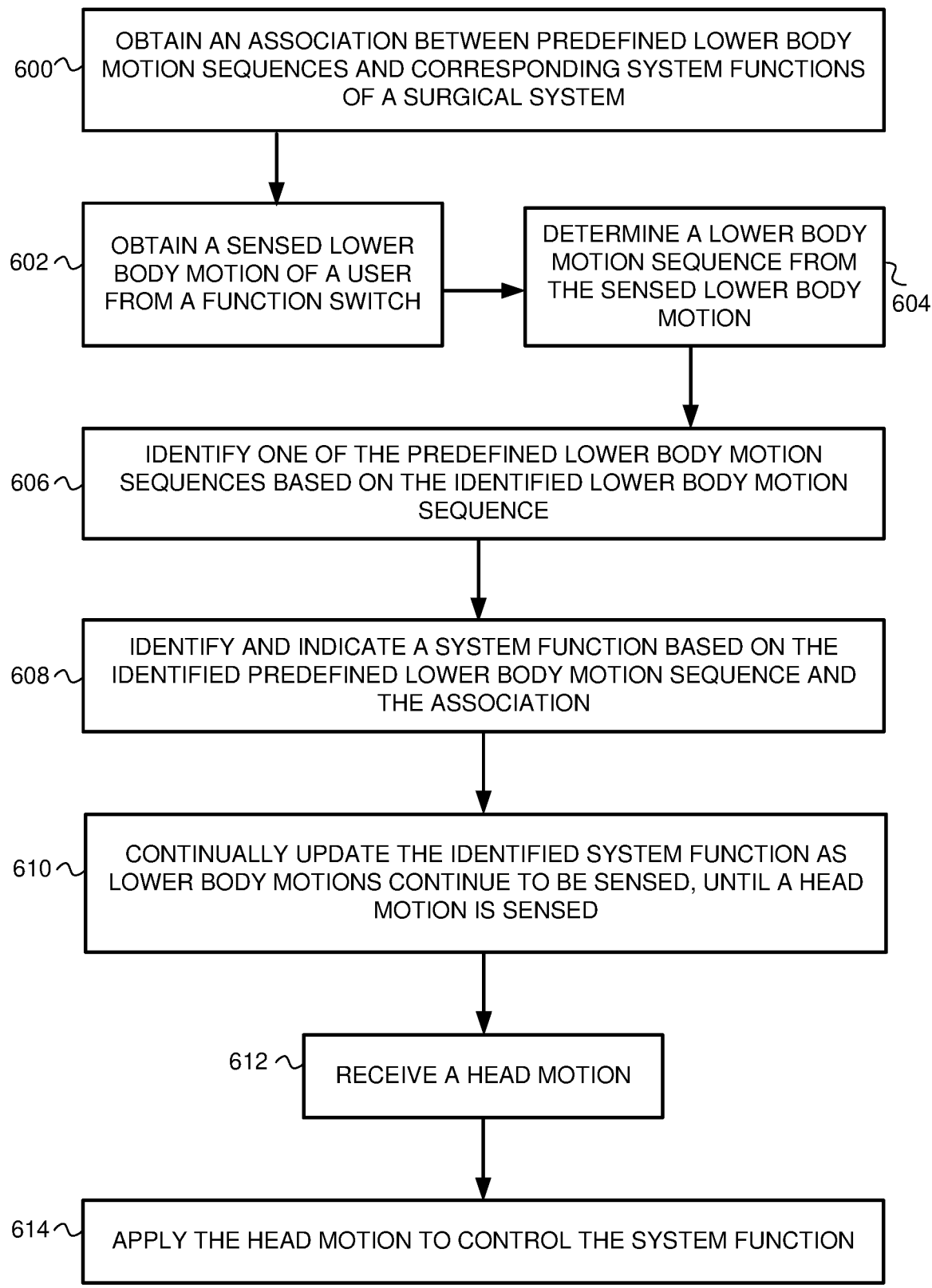
FIG. 6 is a schematic illustration of a method for enabling a plurality of controlling functions of a surgical system, constructed and operative in accordance with another embodiment of the disclosed technique.

Reference is now made to FIG. 6, which is a schematic illustration of a method for enabling a plurality of controlling functions of a surgical system, constructed and operative in accordance with another embodiment of the disclosed technique.

In procedure 600, an association between a plurality of predefined lower body motion sequences of at least one lower body part and a plurality of corresponding system functions of a surgical system is obtained. With reference to FIGS. 1A-1D, an association between multiple predefined lower body motion sequences (e.g. rotations, tilts, etc.) and multiple system functions for controlling surgical system 100 is stored in memory 118D where it can be accessed by processor 118A. In some embodiments, the association is a look-up table mapping certain system functions to certain user motion sequences. In some embodiments, one or more of the predefined lower body motion sequences is an accumulation of multiple lower body motions. In some embodiments, one or more of the predefined lower body motion sequences is a single lower body motion.

In procedure 602, a sensed lower body motion of at least one lower body part of the user is received. With reference to FIGS. 1A-1D, processor 118A of computer 118 receives from function switch 104 a motion of surgeon 120 sensed by sensor 104A of function switch 104. The motion of the lower body part of surgeon 120 may be any of: a tilt, a rotation, a lift, a drop, a turn, a swinging motion, a push, a pull, a twist, a drag, a tap, a press and a swipe motion, and the like. In some embodiments, the lower body motion detected by function switch 104 is a natural body motion that does not require that surgeon 120 memorize numerous buttons or joy stick settings. In some embodiments, the lower body part of surgeon 120 that is sensed is any of: the toe, foot, leg, knee, hip, or waist of surgeon 120. In some embodiments, function switch 104 senses the lower body motion of surgeon 120 along at least one degree of freedom (e.g. axis).

In some embodiments, the processor indicates to the user that the process of function enablement was initiated (or invoked) and/or in process. The indication can either include information regarding the selected function, as described below in step 608, or just include an indication that the enablement process is in process.

In procedure 604, a lower body motion sequence is determined from the sensed motion of the at least one lower body part of the user. With reference to FIGS. 1A-1D, taken together with 2A-2K, function switch 204 senses one or more motions foot 206. Processor 118A of computer 118 receives the sensed motions and determines one or more rotation motion sequences (FIGS. 2A-2C) and one or more tilt motion sequences (FIG. 2J). Processor 118A may use any suitable technique known in the art, such as applying one or more thresholds, filters, deep learning algorithms, and the like to determine the motion sequence from the sensed motion.

In procedure 606, one of the plurality of predefined lower body motion sequences is identified based on the sensed lower body motion sequence. With reference to FIGS. 1A-1D, taken together with FIG. 2K, processor 118A of computer 118 accesses the association stored at memory 118D and identifies a predefined rotate and tilt motion from the motion sequence determined in procedure 604.

In procedure 608, a system function is identified based on the identified one of the plurality of predefined lower body motion sequences and the association. In some embodiments, the identified system function is indicated to the user, and may be continually updated in response to subsequently sensed lower body motions. In some embodiments, the identified function is indicated to the user with non-visual means, such as a tactile indication or sound. With reference to FIGS. 1A-1D together with FIGS. 2A-2K while surgeon 120 rotates function switch 204 with the foot to navigate through the control options displayed on function sliders 220 and 222, processor 118A identifies the selected control options. Processor 118A indicates the selected option, such as by highlighting the menu option, using a tactile or sound indication, and the like. For example, referring to FIGS. 2D-2G, when surgeon 120 rotates foot 206 rightwards, processor 118A identifies and highlights "Zoom" 212, positioned to the right. If surgeon 120 re-orients foot 206 straight, processor 118A identifies and highlights "Illumin" 208, positioned at center. If surgeon 120 rotates foot 206 leftwards, processor 118A identifies and highlights "Focus" 210, positioned to the left. As another example, referring to FIGS. 4H-4J, when surgeon 120 turns foot 406 leftwards on function switch 406, processor 118A highlights the "XY" system function (FIG. 4I), positioned to the left. When surgeon 120 turns foot 406 rightwards on function switch 404, processor 118A highlights the "Z motor" system function, positioned to the right. In some embodiments, processor 118A indicates the identified system function using non-visual means, such as via a vibration motor, or by announcing the system function via a speaker (not shown). Processor 118A continually updates and indicates the selected system function based on sensed motions received from function switch 204 until a head motion is determined.

In some embodiments, the indication indicates only when switching between functions (or group of functions). For example, when the surgeon knows the function layout, a vibration or a beep indicates to the surgeon when the selected function has been switched in response to rotating or tilting the foot on the footrest. For example, this configuration may be used when the amount of rotation or tilt between two functions (or "sliders") is configurable, and when there are more than three functions in a "slider" or more than three "sliders".

In procedure 610, the identified system function is continually updated as lower body motions continue to be sensed, until a head motion is sensed. With reference to FIGS. 1A-1D together with 5A-5I, while surgeon 120 continues to maneuver function switch 504 with foot 506, and prior to moving the head (i.e. the head of surgeon 120 is stationary), function switch 504 continually provides the sensed lower body motions to processor 118A. Processor 118A continues performing procedures 604 to 608 and updates the identified system function, and optionally displaying the function on slider 550 and/or highlighting the identified system function or by tactile or sound indication, until a head motion (e.g. right-left turn 524, or up-down tilt 526) is sensed.

In procedure 612, a head motion is received. With reference to FIGS. 1A-1D together with 5A-5I, head tracker 102 detects a head motion by surgeon 120 (e.g. right-left turn 524, or up-down tilt 526) and provides the tracked head motion to processor 118A. Head tracker 102 may be any combination of: an inertial measuring unit, a camera, an acoustic sensor, a tactile sensor, an electromagnetic sensor, and the like. In some embodiments, head tracker 102 is a wearable device, and may be integrated with HMD 103. In some embodiments, head tracker 102 is a non-wearable device positioned within a trackable range of surgeon 120, such as a camera positioned above surgeon 120 for detecting motion in a predefined direction, such as a sideways turn, and up-down tilt.

In procedure 614, the head motion is applied to control the most recently updated system function. With reference to FIGS. 1A-1D, taken together with FIG. 5F, after invoking menu 510 by maneuvering foot 506 on function switch 504 (FIG. 5A), surgeon 120 turns his head to the right (524) and tilts his head down (526). The rightward and downward head motions 524 and 526 are tracked by head tracker 102 and provided to processor 118A of computer 118. Processor 118A determines two head motions from the tracked head motions, a downward tilt and a rightward turn. Processor 118A selects items from menu 510 to correspond to the head motions.

In some embodiments, applying the head motion to control the system function manifests in an image displayed via HMD 103. Control of the system function is manifested in the image displayed to the surgeon, for example, by selecting which pOCT image to display in an overlay, by display of menus and symbolic overlays (lines, arrows, and the like). In some embodiments, the result of controlling the function manifests in the live video from the camera system (e.g. video acquired by the cameras and/or video generated from other sensors in the camera system, such as an iOCT scanning head). In some embodiments, the result of controlling the system function manifests in the video that is presented to the surgeon also in procedures or in systems without a camera system, such as in VGS procedures or VGS systems.

As another example, turning to FIGS. 5G-5H, surgeon 120 activates "pOCT" 536 by pressing on function switch 504 with foot 506. Once activated, surgeon 120 controls the display of the B-scan image 546 overlaid on the live image 544 using head motions that are provided to processor 118A by head tracker 102. Processor 118A applies the head motions to adjust the position of line 548 on live image 544 and updates the corresponding B-scan image 546 displayed in PIP. For example, if the head tilts upwards (526), processor 118A shifts line 548 upwards in a proportional manner and displays B-scan image 546 corresponding to the updated position of line 548. Similarly if the head tilts downwards, processor 118A shifts line 548 downwards in a proportional manner and updates B-scan image 546 to correspond to the lower position of line 548.

In some embodiments, the updating of the system function is suspended after the head motion has been received and is applied to control the system function.

In some embodiments, subsequently sensed lower body motions are ignored while the head motion is applied to control the identified system function of the surgical system.

In some embodiments, processor 118A deactivates function switch 104 in response to determining that the surgeon's head is in stationary state for a predefined time threshold, allowing surgeon 120 to select and activate a new system function for controlling the surgical system via function switch 104.

In some embodiments, after at least one of: a lapse of a predefined time threshold and the deactivation of function switch 104, processor 118A ceases to apply head motions identified via head tracker 102 to control the identified system function of surgical system 100.

Figure 7:
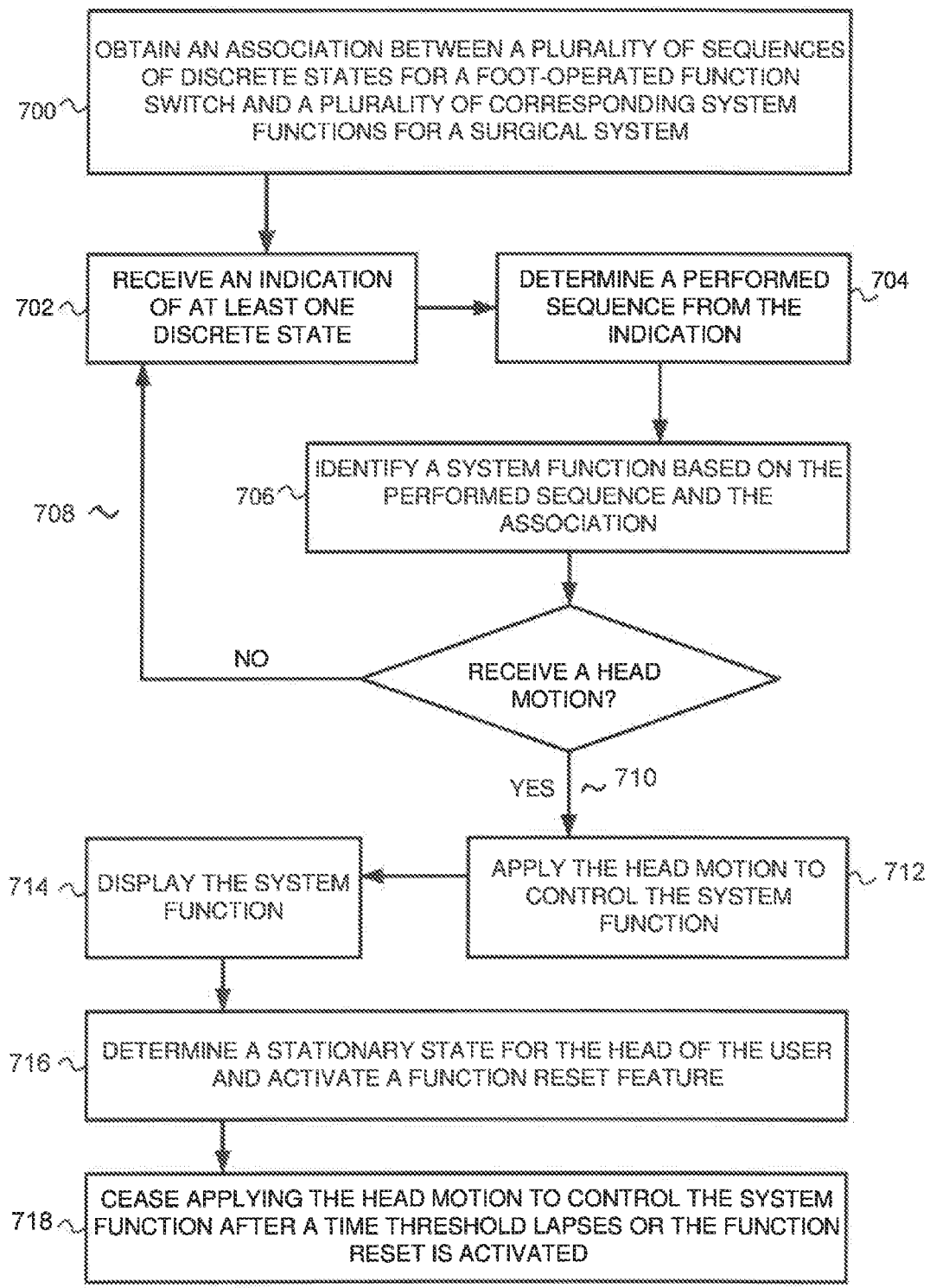
FIG. 7 is a schematic illustration of a method for enabling and controlling functions of a surgical system, constructed and operative in accordance with a further embodiment of the disclosed technique.

Reference is now made to FIG. 7 which is a schematic illustration of a method for enabling and controlling functions of a surgical system, constructed and operative in accordance with a further embodiment of the disclosed technique.

In procedure 700, an association is obtained between a plurality of sequences and a plurality of corresponding system functions of a surgical system. The sequences comprise at least one of multiple discrete states for a foot-operated function switch that is configured to be switched to any of the discrete states by the foot of a user. The sequences may be characterized by one of the discrete states, a predefined duration of one of the discrete states, a subset of the discrete states, an ordered subset of the discrete states, and a repetition of one or more of the discrete states. With reference to FIGS. 1A-1D, processor 118A receives an association between a plurality of predefined sequences and a plurality of corresponding functions for controlling system 100, and stores the association in memory 118D. Each sequence includes at least one of multiple discrete states for function switch 104 configured to be switched by the foot of surgeon 120.

In procedure 702, an indication of at least one of the multiple discrete states is received. With reference to FIGS. 1A-1D, surgeon 120 changes the state of function switch 104 by pressing with the foot. Sensor 104A of function switch 104 senses the pressure and notifies processor 118A of the current state via transmitter 104K and transceiver 118B.

In procedure 704, a performed sequence is determined from the received indication. In some embodiments, the performed sequence is determined from multiple indications received from the function switch of multiple discrete states. With reference to FIGS. 1A-1D, processor 118A receives indications of two consecutive foot presses from function switch within a predefined time frame, such as 2 second. Processor 118A determines a sequence of two presses from the received indications.

In procedure 706, a system function is identified based on the performed sequence and the association. The system function is identified by comparing the performed sequence with the predefined sequences and finding a matching predefined sequence. With reference to FIGS. 1A-1D together with 4A-4C, processor 118A queries the association stored in memory 118D with the performed sequence of procedure 706. Processor 118A compares the performed sequence with the predefined sequences of the association stored in memory 118D. Processor 118A finds a predefined sequence matching the performed sequence and identifies the corresponding system function of displaying second function slider 420.

In procedure 708, updated indications of at least one of the multiple discrete states are continually received, and the performed sequence is continually determined based on the updated indications. With reference to FIGS. 1A-1D and 4E-4G, surgeon 120 continually changes the state of function switch 404 by continually rotating foot 406. For example, surgeon 120 holds foot 406 straight on function switch 404 (FIG. 4E), turns foot 406 leftwards on function switch 404 (FIG. 4F), and turns foot 406 rightwards on function switch 404 (FIG. 4G). Function switch 204 continually sends updated indications to processor 118A as foot 406 is turned and the state is changed. Processor 118A continually updates the current state by querying the association stored in memory 118D for a match. On finding a match, processor 118A continually updates the display of function slider 400, e.g. by highlighting "Focus" in FIG. 4E, corresponding to the straight state for function switch 404, highlighting "Illumin" in FIG. 4F corresponding to the leftward state for function switch 404, and highlighting "Zoom" in FIG. 4G corresponding to the rightwards state of function switch 404.

In procedure 710, a head motion is received. In some embodiments, continually determining the performed sequence and continually identifying the system function are ceased after receiving the head motion. With reference to FIGS. 1A-1D and 4A-4D, the head motion 442 of surgeon 120 is detected by sensor 102A of head tracker 102 and transmitted to processor 118A via transmitter 102J and transceiver 118B. In some embodiments, after receiving the head motion, processor 118A ceases continually identifying the system function based on updated states of function switch 404. Thus, even if surgeon 120 continues to rotate foot 406 on function switch 404, those indications would be ignored.

In procedure 712, the head motion is applied to control the identified system function of the surgical system. In some embodiments, applying the head motion is initiated only after receiving the head motion, and the continual updating is ceased. In some embodiments, subsequently received indications are ignored while the head motion is being applied to control the system function. With reference to FIG. 1A-1D and FIG. 5H, processor 118A applies the up and down head motion 526 of surgeon 120 to move the display of line 548 overlaid on live image 544. Additionally, processor 118A updates pOCT image 546 displayed in PIP in the upper left corner to correspond to the current position of line 548. In some embodiments, while surgeon 120 is maneuvering the position of line 548 with head motions, processor 118A ignores subsequent indications of foot motions on function switch 504.

In procedure 714, the identified system function is displayed. Applying the head motion to control the identified system function is manifested in a displayed image. With reference to FIGS. 1A-1D and 5F-5H, after selection pOCT 536 from submenu for Apps 522 menu item, processor 118A highlights pOCT 536 (FIG. 5F) and displays line 548 and corresponding pOCT image 546 overlaid on live image 544. As surgeon 120 moves the head 526, processor 118A modifies the display by moving line 548 and changing the corresponding pOCT image 546 displayed in PIP.

In some embodiments, applying the head motion to control the system function manifests in an image displayed via HMD 103. Control of the system function is manifested in the image displayed to the surgeon, for example, by selecting which pOCT image to display in an overlay, by display of menus and symbolic overlays (lines, arrows, and the like). In some embodiments, the result of controlling the function manifests in the live video from the camera system (e.g. video acquired by the cameras and/or video generated from other sensors in the camera system, such as an iOCT scanning head). In some embodiments, the result of controlling the system function manifests in the video that is presented to the surgeon also in procedures or in systems without a camera system, such as in VGS procedures or VGS systems.

In procedure 716, a stationary state is determined for the head of the user and the function switch is deactivated in response. With reference to FIGS. 1A-1D and 5I, processor 118A determines that the head of surgeon 120 is stationary for a predetermined time period and deactivates function switch 104.

In procedure 718, applying the head motion to control the identified system function is ceased after at least one of: a lapse of a predefined time threshold, and the deactivation of the function switch. With reference to FIGS. 1A-1D and 5I, after a lapse of a predefined time threshold where no head motion is detected and/or function switch 104 is deactivated, processor 118A ceases to apply subsequently detected head motions to maneuver line 548 and change the pOCT image 546 displayed with live image 544.

It will be appreciated by persons skilled in the art that the disclosed technique is not limited to what has been particularly shown and described hereinabove. Rather the scope of the disclosed technique is defined only by the claims, which follow.

The invention claimed is:

1. A user interface for enabling and controlling functions of a surgical system, comprising:
    a display;
    a foot-operated function switch configured to be switched to any one of multiple discrete states by a foot of a user, wherein the multiple discrete states includes a neutral state and at least two non-neutral states, wherein the at least two non-neutral states are different;
    a head tracker configured to track head motions of said user; and
    a processor coupled to said foot-operated function switch and to said head tracker, said processor configured to:
        obtain an association between each sequence in a plurality of sequences and a corresponding function in a plurality of corresponding system functions of said surgical system, wherein each sequence comprising at least one of said multiple discrete states, and wherein the plurality of sequences comprises at least two different sequences;
        receive at least one indication of at least one of said multiple discrete states from said function switch,
        identify a system function from said plurality of system functions based on said at least one received indication and said association,
        display one or more of said plurality of system functions via one or more function sliders,
        receive a head motion tracked by said head tracker, and
        apply said head motion to control said identified system function of said surgical system.

2. The user interface of claim 1, wherein said processor is configured to determine a performed sequence from said at least one received indication.

3. The user interface of claim 1, wherein said foot-operated function switch is configured to provide a single point of contact with the foot of said user, allowing to switch between said multiple discrete states while maintaining continuous contact between said function switch and said foot of said user via said single point of contact.

4. The user interface of claim 3, wherein said foot-operated function switch has at least one of a rotational degree of freedom and a tilt degree of freedom.

5. The user interface of claim 1, wherein said foot-operated function switch comprises one or more of: a pedal, a footrest, a joystick, a ball held within a socket, an inertial measuring unit, a micro-switch, and an opto-switch.

6. The user interface of claim 1, wherein said processor is configured to display said identified system function via said display.

7. The user interface of claim 1, wherein applying said head motion to control said identified system function is manifested in an image displayed via said display.

8. The user interface of claim 7, further comprising a camera, wherein said image is acquired by said camera.

9. The user interface of claim 1, wherein said display comprises a head mounted display (HMD).

10. The user interface of claim 9, wherein said head tracker is implemented based on tracking said HMD.

11. The user interface of claim 1, wherein at least one of said plurality of sequences comprises one or more of: one of said multiple discrete states, a predefined duration of one of said multiple discrete state, a subset of said multiple discrete states, an ordered subset of said multiple discrete states, and a repetition of one or more of said multiple discrete states.

12. The user interface of claim 1, wherein said processor is configured to continually receive updated indications of at least one of said multiple discrete states from said function switch, continually determine a performed sequence based on said updated indications, and continually identify said system function based on said determined performed sequence and said association, until said head motion is received from said head tracker.

13. A method for enabling and controlling functions of a surgical system, the method comprising:
    obtaining an association between each sequence in a plurality of sequences and a corresponding function of a plurality of corresponding system functions of said surgical system, said each sequence comprising at least one of multiple discrete states for a foot-operated function switch, wherein said foot-operated function switch is configured to be switched to any of said multiple discrete states by a foot of a user, wherein the multiple discrete state includes a neutral state and at least two non-neutral states, wherein the at least two non-neutral states are different, and wherein the plurality of sequences comprises at least two different sequences;

receiving at least one indication of at least one of said multiple discrete states from said function switch;

identifying a system function based on said at least one received indication and said association;

displaying one or more of said plurality of system functions via one or more function sliders;

receiving a head motion tracked by a head tracker; and applying said head motion to control said identified system function of said surgical system.

14. The method of claim 13, further comprising determining a performed sequence from said at least one received indication.

15. The method of claim 13, further comprising displaying said identified system function.

16. The method of claim 13, further comprising continually receiving updated indications of at least one of said multiple discrete states from said function switch, continually determining a performed sequence based on said updated indications, and continually identifying said system function based on said determined performed sequence and said association, until said head motion is received from said head tracker.

17. The method of claim 13, further comprising displaying one or more of said plurality of system functions via one or more output interfaces.

18. The method of claim 13, further comprising terminating said enabling and controlling upon at least one of:

no indications are received from said function switch for a first predetermined period;

no head motions are received from said head tracker for a second predetermined period; and a termination indication is received from said function switch.

* * * * *